(12) United States Patent
Brun et al.

(10) Patent No.: US 7,780,742 B2
(45) Date of Patent: Aug. 24, 2010

(54) COMPOSITION COMPRISING A COMPOUND X AND A COMPOUND Y, AT LEAST ONE OF WHICH IS A SILICONE, AND A HYDROPHOBIC DIRECT DYE

(75) Inventors: Gaëlle Brun, Paris (FR); Luc Gourlaouen, Asnieres (KR)

(73) Assignee: L'Oreal S.A. (FR)

( * ) Notice: Subject to any disclaimer, the term of this patent is extended or adjusted under 35 U.S.C. 154(b) by 282 days.

(21) Appl. No.: 12/004,051

(22) Filed: Dec. 20, 2007

(65) Prior Publication Data

US 2009/0260165 A9    Oct. 22, 2009

Related U.S. Application Data

(60) Provisional application No. 60/897,504, filed on Jan. 26, 2007.

(30) Foreign Application Priority Data

Dec. 20, 2006    (FR) .................... 06 55732

(51) Int. Cl.
*A61Q 5/10*    (2006.01)
(52) U.S. Cl. .............. 8/405; 8/435; 8/552; 8/581; 8/632; 8/675
(58) Field of Classification Search .............. 8/405, 8/435, 552, 581, 632, 675
See application file for complete search history.

(56) References Cited

U.S. PATENT DOCUMENTS

| | | | |
|---|---|---|---|
| 2,643,375 A | 6/1953 | Gant | |
| 2,782,790 A | 2/1957 | Hersh et al. | |
| 2,787,274 A | 4/1957 | Gant et al. | |
| 2,840,087 A | 6/1958 | Hersh | |
| 3,175,993 A | 3/1965 | Weyenberg et al. | |
| 4,344,763 A | 8/1982 | Tolgyesi et al. | |
| 4,772,675 A | 9/1988 | Kiosowski et al. | |
| 4,871,827 A | 10/1989 | Kiosowski et al. | |
| 4,888,380 A | 12/1989 | Kamis et al. | |
| 4,898,910 A | 2/1990 | Kamis et al. | |
| 4,902,499 A | 2/1990 | Bolich, Jr. et al. | |
| 4,906,719 A | 3/1990 | Chu et al. | |
| 4,911,731 A * | 3/1990 | Loveless et al. ............... | 8/405 |
| 4,962,174 A | 10/1990 | Bilgrien et al. | |
| 5,362,486 A | 11/1994 | Nandagiri et al. | |
| 5,811,085 A | 9/1998 | Halloran | |
| 5,968,286 A | 10/1999 | Crudele et al. | |
| 6,165,971 A | 12/2000 | Oppenlander et al. | |
| 6,352,699 B1 | 3/2002 | Mondet et al. | |
| 6,368,581 B1 | 4/2002 | Karlen et al. | |
| 6,432,386 B1 | 8/2002 | Rollat-Corvol et al. | |
| 6,752,984 B2 | 6/2004 | Butts et al. | |
| 7,217,296 B2 | 5/2007 | Pastore et al. | |
| 7,261,744 B2 | 8/2007 | Gourlaouen et al. | |
| 7,303,589 B2 | 12/2007 | Greaves et al. | |
| 2001/0004654 A1 | 6/2001 | Sugimoto et al. | |
| 2002/0076424 A1 | 6/2002 | Birkel et al. | |
| 2002/0155082 A1 | 10/2002 | Richard et al. | |
| 2003/0152543 A1 | 8/2003 | Legrand et al. | |
| 2003/0203978 A1 | 10/2003 | O'Brien et al. | |
| 2004/0052745 A1 | 3/2004 | Bernard et al. | |
| 2005/0011018 A1 | 1/2005 | Greaves et al. | |
| 2005/0028301 A1 | 2/2005 | Pastore | |
| 2005/0232882 A1 | 10/2005 | Bebot et al. | |
| 2006/0010617 A1 | 1/2006 | Gourlaouen et al. | |
| 2006/0031999 A1 | 2/2006 | De Boni et al. | |
| 2006/0045862 A1 | 3/2006 | Tada et al. | |
| 2006/0110351 A1 | 5/2006 | Koehler et al. | |
| 2007/0274941 A9 | 11/2007 | Blin | |
| 2008/0184496 A1 | 8/2008 | Brun et al. | |
| 2008/0233158 A1 | 9/2008 | Blin et al. | |
| 2008/0289647 A1 | 11/2008 | Genain | |
| 2008/0292573 A1 | 11/2008 | Giroud | |
| 2009/0183320 A1 | 7/2009 | Benabdillah | |
| 2009/0214455 A1 | 8/2009 | Blin et al. | |

FOREIGN PATENT DOCUMENTS

| | | |
|---|---|---|
| DE | 200 05 808 | 8/2000 |
| EP | 0 159 628 | 10/1985 |
| EP | 0 465 744 | 1/1992 |
| EP | 0 473 039 | 3/1992 |

(Continued)

OTHER PUBLICATIONS

STIC Search Report dated Mar. 22, 2010.*
Copending Application No. 12/000,886, filed Dec. 18, 2007.
Copending Application No. 12/003,067, filed Dec. 19, 2007.
Copending Application No. 12/003,093, filed Dec. 20, 2007.
Copending Application No. 12/003,125, filed Dec. 20, 2007.
Copending Application No. 12/004,057, filed Dec. 20, 2007.
Copending Application No. 12/004,072, filed Dec. 20, 2007.
Copending Application No. 12/004,103, filed Dec. 20, 2007.
Copending Application No. 12/086,758, filed Jun. 19, 2008.
Copending Application No. 12/097,978, filed Feb. 13, 2009.
English language Abstract of FR 2 760 971, dated Sep. 25, 1998.
English language Abstract of JP 11-349450, dated Dec. 21, 1999.
English language Abstract of WO 2007/071885, dated Jun. 28, 2007.
English language Abstract of WO 2007/071886, dated Jun. 28, 2007.
European Search Report for EP 07 12 3272, dated Jul. 15, 2008.
European Search Report for EP 07 12 3273, dated Nov. 11, 2009.

(Continued)

*Primary Examiner*—Eisa B Elhilo
(74) *Attorney, Agent, or Firm*—Finnegan, Henderson, Farabow, Garrett & Dunner, LLP

(57) ABSTRACT

The present disclosure relates to a composition for coloring keratin fibers comprising in a cosmetically acceptable medium, at least one compound X of polyorganosiloxane comprising siloxane units of a formula (I) and compound Y of organosiloxane comprising at least one alkylhydrogensiloxane unit of a formula (III), wherein when compounds X and Y are placed in contact with each other they react together via a hydrosilyation reaction, at least one hydrophobic direct dye having a log P greater than 2, and optionally at least one organic solvent. The composition of the disclosure makes it possible to obtain varied hues and intense colors on the keratin fibers. Moreover, the coloration is very resistant to external agents, for example, to repeated washing.

21 Claims, No Drawings

FOREIGN PATENT DOCUMENTS

| | | |
|---|---|---|
| EP | 0 865 787 | 9/1998 |
| EP | 0 958 804 | 11/1999 |
| EP | 0 959 066 | 11/1999 |
| EP | 1 101 486 | 5/2001 |
| EP | 1 101 487 | 5/2001 |
| EP | 1 175 893 | 1/2002 |
| EP | 1 190 699 | 3/2002 |
| EP | 1 312 352 | 5/2003 |
| EP | 1 426 027 | 6/2004 |
| EP | 1 433 459 | 6/2004 |
| EP | 1 582 198 | 10/2005 |
| EP | 1 616 558 | 1/2006 |
| EP | 1 938 865 | 7/2008 |
| EP | 1 941 930 | 7/2008 |
| FR | 2 746 102 | 9/1997 |
| FR | 2 760 971 | 9/1998 |
| FR | 2 811 546 | 1/2002 |
| FR | 2 830 189 | 4/2003 |
| FR | 2 851 464 | 8/2004 |
| FR | 2 874 178 | 2/2006 |
| GB | 2 186 890 | 8/1987 |
| GB | 2 401 316 | 11/2004 |
| GB | 2 407 496 | 5/2005 |
| JP | 11-349450 | 12/1999 |
| WO | WO 93/17060 | 9/1993 |
| WO | WO 96/12754 | 5/1996 |
| WO | WO 97/17057 | 5/1997 |
| WO | WO 98/44906 | 10/1998 |
| WO | WO 99/13843 | 3/1999 |
| WO | WO 99/13846 | 3/1999 |
| WO | WO 01/14458 | 3/2001 |
| WO | WO 01/96450 | 12/2001 |
| WO | WO 02/067877 | 9/2002 |
| WO | WO 2004/012691 | 2/2004 |
| WO | WO 2004/084847 | 10/2004 |
| WO | WO 2004/091473 | 10/2004 |
| WO | WO 2005/000856 | 1/2005 |
| WO | WO 2006/028612 | 3/2006 |
| WO | WO 2007/071706 | 6/2007 |
| WO | WO 2007/071885 | 6/2007 |
| WO | WO 2007/071886 | 6/2007 |

OTHER PUBLICATIONS

French Search Report for FR 06/55719, dated Aug. 21, 2007.
French Search Report for FR 06/55726, dated Aug. 8, 2007.
French Search Report for FR 06/55728, dated Oct. 19, 2007.
French Search Report for FR 06/55732, dated Sep. 11, 2007.
French Search Report for FR 06/55753, dated Jul. 18, 2007.
French Search Report for FR 06/55754, dated Jul. 18, 2007.
French Search Report for FR 06/55755, dated Aug. 1, 2007.
French Search Report for FR 06/55756, dated Aug. 1, 2007.
International Search Report for PCT/EP2006/069973, dated Jul. 10, 2007.
International Search Report for PCT/FR2006/051399, dated Jul. 16, 2007.
Kim et al., "Selective Topochemical Photoreaction of Crystallized 2,3-Bis(2-phenylethenyl)-4,5-dicyanopyrazines," *Chemistry Letters*, (1999), (2), pp. 143-144.
Kishi et al., "Development and Application of Latent Hydrosilylation Catalyst [6]: Control of Activity of Platinum Catalyst by Isocyanide Derivatives on the Crosslinking of Silicone Resin via Hydrosilylation," *Internation Journal of Adhesion & Adhesives*, 20, (2000), pp. 253-256.
Kusakabe et al., "Review of Innovative Developments of Silyl-Modified Polymers for Sealant, Adhesive and Coating Applications," *European Coating*, 12-B, (2005), pp. 43-49.
Meylan et al., "Atom/Fragment Contribution Method for Estimating Octanol-Water Partition Coefficients," *Journal of Pharmaceutical Sciences*, vol. 84, No. 1, Jan. 1995, pp. 83-92.
Office Action mailed Aug. 24, 2009, in co-pending U.S. Appl. No. 12/003,125.
Office Action mailed Jun. 11, 2009, in co-pending U.S. Appl. No. 12/000,886.
Probster, "Dichstoffe mit silanvernetzenden Polymeren: Trends und Perspektiven," *Adhesion-Kleben & Dichten*, (2004), 481 (1-2), pp. 12-14.
Schwander et al., "Fluorescent Dyes," *Ullman's Encyclopedia of Industrial Chemistry Release* 2005, 7th Edition, pp. 1-14.
STIC Search Report for U.S. Appl. No. 12/004,051, dated Aug. 18, 2008.
Tomalia et al., "Starburst Dendrimers: Molecular Level Control of Size, Shape, Surface Chemistry, Topology, and Flexibility from Atoms to Macroscopic Matter," Angew. Chem. Int. Ed. Engl., vol. 29, No. 2, (1990), pp. 138-175.

* cited by examiner

COMPOSITION COMPRISING A COMPOUND X AND A COMPOUND Y, AT LEAST ONE OF WHICH IS A SILICONE, AND A HYDROPHOBIC DIRECT DYE

This application claims benefit of U.S. Provisional Application No. 60/897,504, filed Jan. 26, 2007, the contents of which are incorporated herein by reference. This application also claims benefit of priority under 35 U.S.C. §119 to French Patent Application No. FR 06 55732, filed Dec. 20, 2006, the contents of which are also incorporated herein by reference.

The present disclosure relates to a composition for coloring keratin fibers, for example, human keratin fibers such as the hair, comprising a cosmetically acceptable medium; at least one compound X and at least one compound Y, wherein at least one of the compounds X and Y is a silicone compound, and wherein, when X and Y are placed in contact with each other they react together via—a hydrosilylation reaction, a condensation reaction, or a crosslinking reaction in the presence of at least one peroxide; at least one hydrophobic direct dye having a log P greater than 2; and optionally at least one organic solvent.

For many years, it has been desirable to modify the color of hair and in particular to cover up white or gray hair. Several technologies have been developed for this purpose.

The dyeing of keratin fibers, for example, of human keratin fibers such as the hair, with dyeing compositions containing direct dyes, is known. Conventional dyes that are used are, for example, dyes of the nitro benzene, anthraquinone, nitropyridine, azo, xanthene, acridine, azine, or triarylmethane type, or natural dyes. These dyes can be nonionic, anionic, cationic or amphoteric.

These dyes, which are colored and coloring molecules with affinity for keratin fibers, are applied for the length of time required for producing a desired coloration, and are then rinsed.

The resultant colorations are particularly chromatic, but are temporary or semi-permanent due to the nature of the interactions that bind direct dyes to keratin fibers, and their desorption from the surface and/or from the interior of the fiber, which are responsible for their lower dyeing power and their lessened resistance to washing or to perspiration.

Moreover, permanent dyeing of keratin fibers by oxidative dyeing is known. This dyeing technique comprises applying a composition containing dye precursors, such as oxidation bases and couplers, on the keratin fibers. Under the action of an oxidizing agent, these precursors will form one or more colored species in the hair.

The wide variety of molecules employed as oxidation bases and couplers makes it possible to obtain a rich palette of colors. The resultant colorations are permanent, strong, and/or resistant to external agents, for example, to light, to weather, to washing, to sweating, and to rubbing. However, sometimes this type of coloration leads to degradation of the fiber due to the use of an oxidizing agent.

Compositions for treatment of the hair based on compositions comprising electrophilic monomers are also known from French patent application FR 2 833 489. With such a composition it is possible to obtain completely coated hair. However, this coating may not be entirely satisfactory in terms of permanence, and resistance to sebum.

Documents WO 01/96450, GB 2407496, and EP 465 744 describe the use of special reactive silicones for forming a film on the skin. WO 01/96450 and GB 2 407 496 describe a one-part formulation which comprises a polysiloxane having trialkoxyalkylsilyl end groups, a catalyst, a solvent and optionally an alkoxysilane and fillers. These compositions make it possible to obtain a film on the skin by condensation. EP 465 744 describes the use of a polysiloxane with unsaturated aliphatic groups for making medical kits for topical use.

There is still a need to develop new direct dyeing compositions for producing various hues, in particular pastel shades, and which exhibit good resistance, for example, to external agents such as the light, shampoos, and sweat, while preserving the quality of the keratin fibers. In particular, there is a need to develop compositions for permanent dyeing for obtaining coloration having fastness approaching that of oxidative dyeing without one or more of the disadvantages associated with the presence of an oxidizing agent, yet at the same time providing strong and/or chromatic shades.

The present disclosure therefore relates to a composition for dyeing keratin fibers, comprising:
 a cosmetically acceptable medium;
 at least one compound X
 at least one compound Y,
 wherein at least one of the compounds X and Y is a silicone compound, and wherein, when X and Y are placed in contact with each other, they react together by a hydrosilylation reaction, a condensation reaction, or a crosslinking reaction in the presence of at least one peroxide;
 at least one hydrophobic direct dye having a log P greater than 2; and
 optionally at least one organic solvent.

The composition of the present disclosure makes it possible to obtain varied hues and intense colors. Moreover, the coloration obtained may be very resistant to external agents, such as repeated washing.

Furthermore, the hair displays good cosmetic properties, and in particular the individual hairs are kept separate and/or there are fewer or no problems with hairdressing.

The present disclosure also relates to a method of coloring keratin fibers, the method comprising applying to keratin fibers a composition comprising,
 a cosmetically acceptable medium;
 at least one compound X and at least one compound Y, wherein at least one of the compounds X and Y is a silicone compound, and wherein, when placed in contact with each other, X and Y react together via a hydrosilylation reaction, a condensation reaction, or a crosslinking reaction in the presence of at least one peroxide;
 at least one hydrophobic direct dye having a log P greater than 2, and—optionally at least one organic solvent.

Another embodiment of the disclosure relates to a kit for coloring keratin fibers comprising at least two compositions packaged separately, the kit comprising at least two compounds X and Y, which react together when brought into contact with one another, at least one of these compounds being silicone, at least one hydrophobic direct dye whose log P is greater than 2, and optionally at least one organic solvent.

Compounds X and Y

As used herein, "silicone compound" means a compound comprising at least two organosiloxane units. According to at least one embodiment, compounds X and compounds Y are silicone compounds. Compounds X and Y can be aminated or non-aminated. They can include polar groups which may be chosen from the following groups: —COOH; —COO$^-$; —COO—; —OH; —NH$_2$; —NH—; —NR—; —SO$_3$H; —SO$_3^-$; —OCH$_2$CH$_2$—; —O—CH$_2$CH$_2$CH$_2$—; —O—CH$_2$CH(CH$_3$)—; —NR$_3^+$; —SH; —NO$_2$; —I; —Cl; —Br; —CN; —PO$_4^{3-}$; —CONH—; —CONR—; —CONH$_2$; —CSNH—; —SO$_2$—; —SO—; —SO$_2$NH—; —NHCO—; —NHSO$_2$—; —NHCOO—; —OCONH—; —NHCSO—; and —OCSNH—; where R is an alkyl group.

According to another embodiment, at least one of the compounds X and Y is a polymer in which the main chain is formed mainly from organosiloxane units.

Among the silicone compounds described below, some may have both film-forming and adhesive properties, depending for example on their proportion of silicone or depending on whether they are mixed with an additive. Consequently, it is possible to adjust the film-forming properties or the adhesive properties of said compounds according to the intended use, as is the case in particular for the so-called "room temperature vulcanization" reactive elastomeric silicones.

Compounds X and Y can react with each other at a temperature ranging from room temperature to 180° C. In some embodiments, compounds X and Y can react with each other at room temperature (20±5° C.) and atmospheric pressure, in at least one embodiment in the presence of a catalyst, by a hydrosilylation reaction, or a condensation reaction, or a crosslinking reaction in the presence of at least one peroxide.

1. Compounds X and Y—Hydrosilylation Reaction

According to one embodiment, compounds X and Y react by hydrosilylation, a reaction that can be represented in a simplified form as follows:

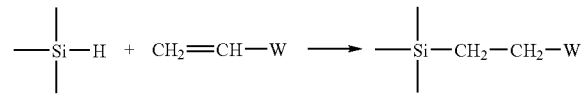

wherein W is a carbon chain and/or silicone chain containing at least one unsaturated aliphatic group.

In this embodiment, compound X can be chosen from silicone compounds containing at least two unsaturated aliphatic groups. As an example, compound X can comprise a silicone main chain having unsaturated aliphatic groups that are pendant from the main chain (side group) or that are located at the ends of the main chain of the compound (end group). These compounds will be called, hereinafter, "polyorganosiloxanes comprising unsaturated aliphatic groups."

According to one embodiment, compound X is chosen from polyorganosiloxanes comprising at least two unsaturated aliphatic groups, for example two or three vinyl or allyl groups, each attached to a silicon atom.

According to another embodiment, compound X is chosen from polyorganosiloxanes comprising siloxane units of formula:

$$R_m R'SiO_{(3-m)/2} \quad (I)$$

wherein:

R is a linear or cyclic, monovalent hydrocarbon group having from 1 to 30 carbon atoms, for example, from 1 to 20 carbon atoms, and further, for example, from 1 to 10 carbon atoms, for example a short-chain alkyl radical, comprising, for example, from 1 to 10 carbon atoms, such as a methyl radical or alternatively a phenyl group, and in one embodiment is a methyl radical;

m is 1 or 2; and

R' is chosen from:

an unsaturated aliphatic hydrocarbon group having from 2 to 10, for example, from 2 to 5 carbon atoms, such as a vinyl group, an allyl group, or mixtures thereof, or a group —R''—CH=CHR''' in which R'' is a divalent aliphatic hydrocarbon chain, having from 1 to 8 carbon atoms, joined to the silicon atom, and R''' is a hydrogen atom or an alkyl radical having from 1 to 4 carbon atoms, wherein in one embodiment R''' is a hydrogen atom; and an unsaturated cyclic hydrocarbon group having from 5 to 8 carbon atoms, for example, a cyclohexenyl group.

In one embodiment, R' is an unsaturated aliphatic hydrocarbon group, such as a vinyl group.

According to another embodiment, compound X is a polyorganosiloxane also comprising units of formula:

$$R_n SiO_{(4-n)/2} \quad (II)$$

wherein R is a group as defined above, and n is 1, 2 or 3.

According to another embodiment, compound X can be a silicone resin comprising at least two ethylenic unsaturations, wherein said resin can react with compound Y by hydrosilylation. One non-limiting example of such resins are those of the MQ or MT type, which have unsaturated reactive ends —CH=CH$_2$. These resins are crosslinked organosiloxane polymers.

These silicone resins are known by the name of "MDTQ", the resin being described according to the different siloxane monomeric units that it contains, each of the letters "MDTQ" characterizing a type of unit.

The letter M represents a monofunctional unit of formula $(CH_3)_3SiO_{1/2}$, the silicon atom being joined to a single oxygen atom in the polymer containing said unit.

The letter D represents a bifunctional unit $(CH_3)_2SiO_{2/2}$ in which the silicon atom is joined to two oxygen atoms.

The letter T represents a trifunctional unit of formula $(CH_3)SiO_{3/2}$.

In M, D, and T defined above, at least one of the methyl groups can be substituted with an R group, which is different from the methyl group, such as a hydrocarbon radical (i.e., alkyl group) having from 2 to 10 carbon atoms, a phenyl group, or a hydroxyl group.

Finally, the letter Q represents a tetrafunctional unit $SiO_{4/2}$ in which the silicon atom is joined to four hydrogen atoms, wherein the silicon atom is attached to the rest of the polymer. Examples of these resins are silicone resins of the MT type, such as poly(phenyl-vinylsilsesquioxane), for example, those marketed under the reference SST-3PV1 by the company Gelest.

In at least one embodiment, compound X comprises from 0.01 to 1 wt. % unsaturated aliphatic groups.

In at least one embodiment, compound X is chosen from polyorganopolysiloxanes, for example a polyorganosiloxane comprising siloxane units of formula (I) and optionally formula (II), described above.

In at least one embodiment, compound Y has at least two free Si—H groups (hydrogen silane groups).

In another embodiment, compound Y can be chosen from organosiloxanes comprising at least one alkylhydrogenosiloxane unit of the following formula:

$$R_p HSiO_{(3-p)/2} \quad (III)$$

wherein:

R is a linear or cyclic, monovalent hydrocarbon group having from 1 to 30 carbon atoms, for example an alkyl radical having from 1 to 30 carbon atoms, such as an alkyl radical having from 1 to 20 carbon atoms, or, for example, from 1 to 10 carbon atoms, such as a methyl radical, or alternatively a phenyl group, and p is 1 or 2. In one embodiment, R is a hydrocarbon group, for example, a methyl group.

The organosiloxane compound Y comprising alkylhydrogenosiloxane units can further comprise units of formula:

(II)

as defined above.

In at least one embodiment, compound Y can be a silicone resin comprising at least one unit selected from the units M, D, T, Q as defined above and comprising at least one Si—H group such as the poly(methyl-hydridosilsesquioxane) marketed under the reference SST-3 MH1.1 by the company Gelest.

In at least one embodiment, the organosiloxane compound Y comprises from 0.5 to 2.5 wt. % Si—H groups.

In at least one embodiment, the radicals R in formulae (I), (II), and (III) above are all methyl groups.

In at least one embodiment, the organosiloxane compound Y comprises end groups of formula $(CH_3)_3SiO_{1/2}$.

In another embodiment, the organosiloxane compound Y comprises at least two alkylhydrogenosiloxane units of formula $(H_3C)(H)SiO$ and optionally comprise units of formula $(H_3C)_2SiO$. These organosiloxane compounds with hydrogen silane groups are described for example in European Patent EP 0 465 744.

According to at least one embodiment, compound X is chosen from organic oligomers or polymers (organic is defined as compounds in which the main chain is not a silicone, for example, compounds not containing silicon atoms), and from hybrid organic/silicone polymers or oligomers, each of said oligomers or polymers having at least two reactive unsaturated aliphatic groups, and compound Y being chosen from hydrogenosiloxanes described above.

Compound X, when of organic nature, can, in at least one embodiment, be chosen from vinylic, (meth)acrylic polymers or oligomers, polyesters, polyurethanes and/or polyureas, polyethers, perfluoropolyethers, polyolefins such as polybutene, polyisobutylene, dendrimers, and hyperbranched organic polymers, and mixtures thereof.

In at least one embodiment, the organic polymer or the organic moiety of the hybrid polymer can be chosen from the following polymers:

a) polyesters with ethylenic unsaturation(s) This is a group of polymers of the polyester type having at least two ethylenic double bonds, randomly distributed in the main chain of the polymer. These unsaturated polyesters are obtained by polycondensation of a mixture:

of linear or branched aliphatic or cycloaliphatic dicarboxylic acids having, in at least one embodiment, from 3 to 50 carbon atoms, for example, from 3 to 20 carbon atoms, or for example, from 3 to 10 carbon atoms, such as adipic acid or sebacic acid; of aromatic dicarboxylic acids having, in at least one embodiment, from 8 to 50 carbon atoms, for example, from 8 to 20 carbon atoms, or, for example, from 8 to 14 carbon atoms, such as phthalic acids, for example, terephthalic acid; and/or of dicarboxylic acids obtained from dimers of fatty acids with ethylenic unsaturations such as the dimers of oleic or linoleic acids described in European Patent Application EP-A-959 066 (paragraph [0021]) marketed under the names Pripol® by the company Unichema or Empol® by the company Henkel, and all said diacids are free from polymerizable ethylenic double bonds;

of inear or branched aliphatic or cycloaliphatic diols having, in at least one embodiment, from 2 to 50 carbon atoms, for example, from 2 to 20 carbon atoms, or, for example, from 2 to 10 carbon atoms, such as ethylene glycol, diethylene glycol, propylene glycol, 1,4-butanediol or cyclohexanedimethanol; of aromatic diols having from 6 to 50 carbon atoms, for example, from 6 to 20 carbon atoms, or, for example, from 6 to 15 carbon atoms, such as bisphenol A and bisphenol B; and/or of diol dimers resulting from reduction of dimers of fatty acids as defined above; and of at least one dicarboxylic acid or anhydride thereof having at least one polymerizable ethylenic double bond and having from 3 to 50 carbon atoms, for example, from 3 to 20 carbon atoms, or, for example, from 3 to 10 carbon atoms, such as maleic acid, fumaric acid or itaconic acid.

b) polyesters with (meth)acrylate side and/or end groups These comprise a group of polymers of the polyester type obtained by polycondensation of a mixture:

of linear or branched aliphatic or cycloaliphatic dicarboxylic acids having, in at least one embodiment, from 3 to 50 carbon atoms, for example, from 3 to 20 carbon atoms, or, for example, from 3 to 10 carbon atoms, such as adipic acid or sebacic acid; of aromatic dicarboxylic acids having, in at least one embodiment, from 8 to 50 carbon atoms, for example, from 8 to 20 carbon atoms, or, for example, from 8 to 14 carbon atoms, such as phthalic acids, terephthalic acid; and/or of dicarboxylic acids obtained from dimers of fatty acids with an ethylenic unsaturation such as the dimers of oleic or linoleic acids described in European patent application EP-A-959 066 (paragraph [0021]), marketed under the names Pripol® by the company Unichema or Empol® by the company Henkel, and all said diacids are free from polymerizable ethylenic double bonds;

of linear or branched aliphatic or cycloaliphatic diols having, in at least one embodiment, from 2 to 50 carbon atoms, for example, from 2 to 20 carbon atoms, or, for example, from 2 to 10 carbon atoms, such as ethylene glycol, diethylene glycol, propylene glycol, 1,4-butanediol or cyclohexanedimethanol, of aromatic diols having from 6 to 50 carbon atoms, for example, from 6 to 20 carbon atoms, or, for example, from 6 to 15 carbon atoms, such as bisphenol A and bisphenol B; and of at least one ester of (meth)acrylic acid and a diol or polyol having from 2 to 20 carbon atoms, for example, from 2 to 6 carbon atoms, such as 2-hydroxyethyl (meth)acrylate, 2-hydroxypropyl(meth)acrylate, and glycerol methacrylate.

These polyesters differ from those described above in section a) in that the ethylenic double bonds are not located in the main chain, but on side groups or at the end of the chains. These ethylenic double bonds are those of the (meth)acrylate groups present in the polymer.

Some non-limiting examples of these polyesters are marketed for example by the company UCB under the names EBECRYL® (EBECRYL® 450: molar mass 1600, on average 6 acrylate functional groups per molecule, EBECRYL® 652: molar mass 1500, on average 6 acrylate functional groups per molecule, EBECRYL® 800: molar mass 780, on average 4 acrylate functional groups per molecule, EBECRYL® 810: molar mass 1000, on average 4 acrylate functional groups per molecule, and EBECRYL® 50 000: molar mass 1500, on average 6 acrylate functional groups per molecule).

c) polyurethanes and/or polyureas with (meth)acrylate groups
obtained by polycondensation:
of aliphatic, cycloaliphatic and/or aromatic diisocyanates, triisocyanates and/or polyisocyanates having, in at least one embodiment, from 4 to 50, for example, from 4 to 30 carbon atoms, such as hexamethylenediisocyanate, isophoronediisocyanate, toluenediisocyanate, diphenylmethanediisocyanate or the isocyanurates of formula:

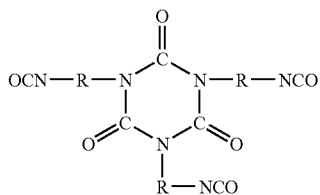

resulting from the trimerization of three diisocyanate molecules OCN—R—CNO, where R is a linear, branched or cyclic hydrocarbon radical with from 2 to 30 carbon atoms;
of polyols, such as diols, free from polymerizable ethylenic unsaturations, such as 1,4-butanediol, ethylene glycol or trimethylolpropane, and/or of polyamines, such as aliphatic, or cycloaliphatic, and/or aromatic diamines having from 3 to 50 carbon atoms, such as ethylenediamine or hexamethylenediamine; and
of at least one ester of (meth)acrylic acid and of a diol or polyol having from 2 to 20 carbon atoms, for example, from 2 to 6 carbon atoms, such as 2-hydroxyethyl (meth)acrylate, 2-hydroxypropyl(meth)acrylate, and glycerol methacrylate.

Some examples of polyurethanes/polyureas with acrylate groups are marketed under the name SR 368 (tris(2-hydroxyethyl)isocyanurate-triacrylate) or CRAYNOR® 435 by the company CRAY VALLEY, or under the name EBECRYL® by the company UCB (EBECRYL® 210: molar mass 1500, 2 acrylate functional groups per molecule, EBECRYL® 230: molar mass 5000, 2 acrylate functional groups per molecule, EBECRYL® 270: molar mass 1500, 2 acrylate functional groups per molecule, EBECRYL® 8402: molar mass 1000, 2 acrylate functional groups per molecule, EBECRYL® 8804: molar mass 1300, 2 acrylate functional groups per molecule, EBECRYL® 220: molar mass 1000, 6 acrylate functional groups per molecule, EBECRYL® 2220: molar mass 1200, 6 acrylate functional groups per molecule, EBECRYL® 1290: molar mass 1000, 6 acrylate functional groups per molecule, and EBECRYL® 800: molar mass 800, 6 acrylate functional groups per molecule).

Some examples of water-soluble aliphatic diacrylate polyurethanes are marketed under the names EBECRYL® 2000, EBECRYL® 2001 and EBECRYL® 2002, and the diacrylate polyurethanes in aqueous dispersion marketed under the trade names IRR® 390, IRR® 400, IRR® 422, and IRR® 424 by the company UCB.

d) polyethers with (meth)acrylate groups obtained by esterification, by (meth)acrylic acid, of the hydroxyl end groups of homopolymers or of copolymers of $C_1$-$C_4$ alkylene glycols, such as polyethylene glycol, polypropylene glycol, copolymers of ethylene oxide and propylene oxide, for example, having a weight-average molecular weight below 10 000, polyethoxylated, or polypropoxylated trimethylolpropane.

Some examples of di(meth)acrylate polyoxyethylenes of suitable molar mass are marketed under the names SR 259, SR 344, SR 610, SR 210, SR 603 and SR 252 by the company CRAY VALLEY or under the name EBECRYL® 11 by UCB. Polyethoxylated trimethylolpropane triacrylates are marketed for example under the names SR 454, SR 498, SR 502, SR 9035, and SR 415 by the company CRAY VALLEY or under the name EBECRYL® 160 by the company UCB. Polypropoxylated trimethylolpropane triacrylates are marketed for example under the names SR 492 and SR 501 by the company CRAY VALLEY.

e) epoxyacrylates obtained by reaction between
at least one diepoxide chosen, for example, from:
(i) diglycidyl ether of bisphenol A,
(ii) a diepoxy resin resulting from reaction between diglycidyl ether of bisphenol A and epichlorohydrin,
(iii) an epoxyester resin with α,ω-diepoxy end groups resulting from the condensation of a dicarboxylic acid having from 3 to 50 carbon atoms with a stoichiometric excess of (i) and/or (ii),
(iv) an epoxyether resin with α,ω-diepoxy end groups resulting from the condensation of a diol having from 3 to 50 carbon atoms with a stoichiometric excess of (i) and/or (ii),
(v) natural or synthetic oils bearing at least 2 epoxide groups, such as epoxidized soya oil, epoxidized linseed oil, and epoxidized vernonia oil,
(vi) a phenol-formaldehyde polycondensate (Novolac® resin), in which the end groups and/or side groups have been epoxidized,
and
at least one carboxylic acid or carboxylic polyacid having at least one α,β ethylenic double bond of the carboxyl group such as (meth)acrylic acid or crotonic acid or esters of (meth)acrylic acid and of a diol or polyol having from 2 to 20 carbon atoms, for example, from 2 to 6 carbon atoms, such as 2-hydroxyethyl(meth)acrylate.

Such polymers are marketed, for example, under the names SR 349, SR 601, CD 541, SR 602, SR 9036, SR 348, CD 540, SR 480, and CD 9038 by the company CRAY VALLEY, under the names EBECRYL® 600 and EBECRYL® 609, EBECRYL® 150, EBECRYL® 860, and EBECRYL® 3702 by the company UCB and under the names PHOTOMER® 3005 and PHOTOMER® 3082 by the company HENKEL.

f) alkyl) ($C_{1-50}$ alkyl) poly(meth)acrylates, said alkyl group being linear, branched, or cyclic, having at least two functional groups with an ethylenic double bond carried by the lateral and/or terminal hydrocarbon chains.

Such copolymers are marketed, for example, under the names IRR® 375, OTA® 480 and EBECRYL® 2047 by the company UCB.

g) Polyolefins such as polybutene, polyisobutylene.

h) perfluoropolyethers with acrylate groups obtained by esterification, for example by (meth)acrylic acid, of perfluoropolyethers bearing hydroxyl side and/or end groups.

These α,ω-diol perfluoropolyethers are described, for example, in European Patent Application EP-A-1057849 and are marketed, for example, by the company AUSIMONT under the name FOMBLIN® Z DIOL.

i) dendrimers and hyperbranched polymers having (meth)acrylate or (meth)acrylamide end groups obtained, respectively, by esterification or amidation of dendrimers and of hyperbranched polymers with hydroxyl or amino terminal functional groups, by (meth)acrylic acid.

The dendrimers (from the Greek dendron=tree) are treelike polymeric molecules, i.e., highly branched, invented by D. A. Tomalia and his team at the beginning of the 1990s (Donald A. Tomalia et al., Angewandte Chemie, Int. Engl. Ed., Vol. 29, No. 2, pages 138-175). They are structures built around a generally polyvalent central unit. Branched chain extending units are arranged according to a perfectly defined structure around this central unit, thus giving rise to symmetrical, monodispersed macromolecules having a well-defined chemical and stereochemical structure. Dendrimers of the polyamidoamine type are marketed, for example, under the name STARBURST® by the company DENDRITECH.

The hyperbranched polymers are polycondensates, generally of the polyester, polyamide or polyethyleneamine type, obtained from multifunctional monomers, which have a tree-like structure similar to that of the dendrimers, but far less regular than the latter (see, for example, International Patent Applications WO-A-93/17060 and WO 96/12754).

The company PERSTORP markets hyperbranched polyesters under the name BOLTORN®. Hyperbranched polyethyleneamines are available under the name COMBURST® from the company DENDRITECH. Hyperbranched poly(esteramide)s with hydroxyl end groups are marketed by the company DSM under the name HYBRANE®.

These dendrimers and hyperbranched polymers, esterified or amidated by acrylic and/or methacrylic acid, differ from the polymers described in sections a) to h) above by the large number of ethylenic double bonds present. This increased functionality, generally greater than 5, makes them useful in enabling them to act as a "crosslinking node", i.e., a multiple crosslinking site.

It is therefore possible to use these dendritic and hyperbranched polymers in association with one or more of the above polymers and/or oligomers a) to h).

1a. Additional Reactive Compounds

According to at least one embodiment, the composition according to the disclosure can further comprise an additional reactive compound such as:

organic or mineral particles having on their surface at least two unsaturated aliphatic groups—for example, silicas surface-treated, for example, with silicone compounds with vinylic groups such as for example cyclotetramethyltetravinylsiloxane-treated silica, or silazane compounds such as hexamethyldisilazane.

1b. Catalyst

The hydrosilylation reaction can be carried out in the presence of a catalyst, which can be present in the composition according to the disclosure, and may, in at least one embodiment, be chosen from platinum-based and tin-based catalysts comprising platinum or tin. Examples include, but are not limited to, platinum-based catalysts deposited on a support of silica gel or powdered charcoal, platinum chloride, salts of platinum and chloroplatinic acids. In at least one embodiment, the chloroplatinic acids are used in hexahydrate or anhydrous form, which are easily dispersible in organosilicone media.

Examples of platinum complexes include those based on chloroplatinic acid hexahydrate and divinyl tetramethyldisiloxane.

The catalyst can be present in the composition in an amount ranging from 0.0001 wt. % to 20 wt. %, relative to the total weight of the composition.

The composition of the disclosure can also include polymerization inhibitors or retarders, such as inhibitors of the catalyst, in order to increase the stability of the composition over time or to delay polymerization. Examples of these include cyclic polymethylvinylsiloxanes, such as tetravinyl tetramethyl cyclotetrasiloxane, and acetylenic alcohols, for example, volatile acetylenic alcohols, such as methylisobutynol.

In some embodiments, the composition of the disclosure may include ionic salts. The presence of ionic salts, such as sodium acetate, in the composition can have an influence on the rate of polymerization of the compounds.

In one embodiment, compounds X and Y are chosen from silicone compounds that can react by hydrosilylation; for example, compound X is chosen from polyorganosiloxanes comprising units of formula (I) described above and compound Y is chosen from organosiloxanes comprising alkylhydrogenosiloxane units of formula (III) described above.

According to one embodiment, compound X is a polydimethylsiloxane with vinylic end groups, and compound Y is methylhydrogenosiloxane.

As examples of a combination of compounds X and Y reacting by hydrosilylation, there may be mentioned Dow Corning: DC 7-9800 Soft Skin Adhesive parts A & B, as well as the following mixtures A and B produced by Dow Corning:

Mixture A:

| Ingredient (INCI Name) | CAS No. | Content (wt. %) | Function |
|---|---|---|---|
| Dimethyl Siloxane, Dimethylvinylsiloxy-terminated | 68083-19-2 | 55-95 | Polymer |
| Silica Silylate | 68909-20-6 | 10-40 | Filler |
| 1,3-Diethenyl-1,1,3,3-Tetramethyldisiloxane complexes | 68478-92-2 | Trace | Catalyst |
| Tetramethyldivinyldisiloxane | 2627-95-4 | 0.1-1 | Polymer |

Mixture B:

| Ingredient (INCI Name) | CAS No. | Content (wt. %) | Function |
|---|---|---|---|
| Dimethyl Siloxane, Dimethylvinylsiloxy-terminated | 68083-19-2 | 55-95 | Polymer |
| Silica Silylate | 68909-20-6 | 10-40 | Filler |
| Dimethyl, Methylhydrogen Siloxane, trimethylsiloxy-terminated | 68037-59-2 | 1-10 | Polymer |

2. Compounds X and Y—Condensation Reaction

According to this embodiment, compounds X and Y react by condensation, either in the presence of water (hydrolysis) by reaction of two compounds bearing alkoxysilane groups, or by so-called "direct" condensation by reaction of a compound bearing alkoxysilane group(s) and a compound bearing silanol group(s) or by reaction of two compounds bearing silanol group(s).

When condensation is carried out in the presence of water, the water can, for example, be the ambient humidity, the residual water of the keratin fibers, or water supplied by an external source, for example, by prior moistening of the keratin fibers (for example with an atomizer).

In this method of reaction by condensation, compounds X and Y, which may be identical or different, can be chosen from silicone compounds in which the main chain comprises at least two alkoxysilane groups and/or at least two silanol (Si—OH) groups, lateral and/or terminal.

According to one embodiment, compound X and/or Y are chosen from polyorganosiloxanes comprising at least two alkoxysilane groups. An "alkoxysilane" group, as used herein, means a group comprising at least one —Si—OR moiety, R being an alkyl group having from 1 to 6 carbon atoms.

In another embodiment, compounds X and Y are chosen from polyorganosiloxanes having alkoxysilane end groups, for example, those comprising at least 2 alkoxysilane end groups, such as trialkoxysilane end groups.

In another embodiment, compounds X and/or Y comprise mainly units of formula:

$$R^9{}_s SiO_{(4-s)/2}, \quad (IV)$$

wherein each $R^9$ is, independently, a radical chosen from alkyl groups having from 1 to 6 carbon atoms, phenyl groups, and fluorinated alkyl groups, and s is 0, 1, 2 or 3. In a further embodiment, each $R^9$ is, independently, an alkyl group with from 1 to 6 carbon atoms. Examples of alkyl groups, include, but are not limited to, methyl, propyl, butyl, and hexyl, or mixtures thereof. In one embodiment the alkyl groups are chosen from methyl and ethyl. An example of a fluoroalkyl group is a 3,3,3-trifluoropropyl group.

According to another embodiment, compounds X and Y, which may be identical or different, are polyorganosiloxanes comprising units of formula:

$$(R^9{}_2 SiO_2)_f- \quad (V)$$

wherein $R^9$ is a group as defined above, and in a further embodiment is a methyl radical, and f is an integer such that the polymer has a viscosity at 25° C. in the range from 0.5 to 3000 Pa·s, for example, in the range from 5 to 150 Pa·s and/or f is an integer from 2 to 5000, for example, from 3 to 3000, or, for example, from 5 to 1000.

These polyorganosiloxane compounds X and Y of formula (I) have at least two trialkoxysilane end groups per molecule of polymer, said groups having the following formula:

$$-ZSiR^1{}_x(OR)_{3-x}, \quad (VI)$$

wherein:

each radical R is, independently, chosen from methyl, ethyl, n-propyl, isopropyl, n-butyl, sec-butyl, and isobutyl groups, for example, methyl and ethyl groups, $R^1$ is a methyl or ethyl group, x is 0 or 1, and Z is chosen from: divalent hydrocarbon groups without an ethylenic unsaturation and having from 1 to 18 carbon atoms, for example, from 2 to 18 carbon atoms (alkylene groups), combinations of divalent hydrocarbon radicals, and siloxane segments of the following formula (IX):

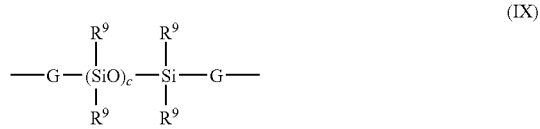

$R^9$ is a group as defined above, G is a divalent hydrocarbon radical without an ethylenic unsaturation and having from 1 to 18 carbon atoms, for example, from 2 to 18 carbon atoms, and c is an integer in the range from 1 to 6.

Z and G can be chosen from alkylene groups such as methylene, ethylene, propylene, butylene, pentylene, hexylene, and arylene groups, such as phenylene. In one embodiment, Z is an alkylene group, for example, an ethylene group.

These polymers can have on average at least 1.2 end groups or terminal trialkoxysilane chains per molecule, and, in at least one embodiment, on average at least 1.5 trialkoxysilane end groups per molecule. These polymers can have at least 1.2 trialkoxysilane end groups per molecule, and some can have other types of end groups such as end groups of formula $CH_2=CH-SiR^9{}_2-$ or of formula $R^6{}_3-Si-$, in which $R^9$ is a group as defined above and each $R^6$ group is independently chosen from alkyl groups having from 1 to 6 carbon atoms, phenyl groups, fluorinated alkyl groups, and vinyl groups. Some examples of these end groups include the trimethoxysilane, triethoxysilane, vinyldimethoxysilane and vinylmethyloxyphenylsilane groups.

Such polymers are described, for instance, in U.S. Pat. No. 3,175,993, U.S. Pat. No. 4,772,675, U.S. Pat. No. 4,871,827, U.S. Pat. No. 4,888,380, U.S. Pat. No. 4,898,910, U.S. Pat. No. 4,906,719 and U.S. Pat. No. 4,962,174, the contents of which are incorporated by reference herein.

In at least one embodiment, compounds X and/or Y may be a polymer of formula:

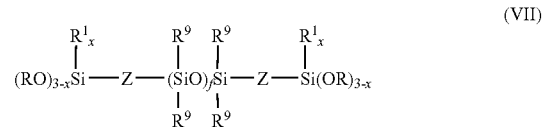

wherein R, $R^1$, $R^9$, Z, x and f are as defined above.

In other embodiments, compounds X and/or Y can also comprise a mixture of a polymer of formula (VII) above with polymers of the formula (VIII):

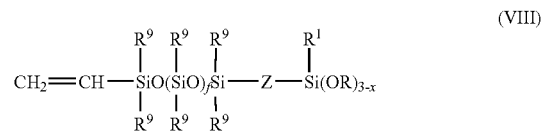

wherein R, $R^1$, $R^9$, Z, x and f are as defined above.

When the polyorganosiloxane compounds X and/or Y with alkoxysilane group(s) comprise a mixture of polymers of formula (VII) and (VIII), the various polyorganosiloxanes are present in an amount such that the organosilyl end chains are less than 40%, for example, less than 25%, of the number of terminal chains.

In one embodiment, the polyorganosiloxane compounds X and/or Y are those of formula (VII) described above. Examples of these compounds are described in International Application No. WO 01/96450.

As mentioned above, compounds X and Y as used herein may be identical or different.

According to one embodiment, one of the two reactive compounds X or Y is of a silicone nature and the other is of an organic nature. For example, compound X is chosen from organic oligomers or polymers and hybrid organic/silicone oligomers or polymers, each of said polymers or oligomers comprising at least two alkoxysilane groups, and Y is chosen from silicone compounds such as the polyorganosiloxanes described above. In some embodiments, the organic oligomers or polymers are chosen from vinylic, (meth)acrylic oligomers or polymers, polyesters, polyamides, polyurethanes and/or polyureas, polyethers, polyolefins, perfluoropolyethers, dendrimers and hyperbranched organic polymers, or mixtures thereof.

The vinylic or (meth)acrylic organic polymers, bearing alkoxysilane side groups, can, for example, be obtained by copolymerization of at least one vinylic or (meth)acrylic organic monomer with a (meth)acryloxypropyltrimethoxysilane, a vinyl trimethoxysilane, a vinyltriethoxysilane, an allyltrimethoxysilane, etc.

Non-limiting mention may be made, for example, of the (meth)acrylic polymers described in KUSABE. M, Pitture e Verniei—European Coating; 12-B, pages 43-49, 2005, and, for example, the polyacrylates with alkoxysilane groups designated MAX from Kaneka or those described in PROBSTER, M, in Adhesion-Kleben & Dichten, 2004, 481 (1-2), pages 12-14.

The organic polymers resulting from polycondensation or from polyaddition, such as polyesters, polyamides, polyurethanes and/or polyureas, polyethers, and bearing alkoxysilane side and/or end groups, may result for example from the reaction of an oligomeric prepolymer such as described above with one of the following silane co-reactants bearing at least one alkoxysilane group, such as aminopropyltrimethoxysilane, aminopropyltriethoxysilane, aminoethylaminopropyltrimethoxysilane, glycidoxypropyltrimethoxysilane, glycidoxypropyltriethoxysilane, epoxycyclohexylethyltrimethoxysilane, and mercaptopropyltrimethoxysilane.

Examples of polyethers and polyisobutylenes with alkoxysilane groups are described in KUSABE, M., in Pitture e Verniei—European Coating; 12-B, pages 43-49, 2005. Some examples of polyurethanes with alkoxysilane end groups are described in PROBSTER, M., Adhesion-Kleben & Dichten, 2004, 481 (1-2), pages 12-14 or in LANDON, S., Pitture e Verniei Vol. 73, No. 11, pages 18-24, 1997 or in HUANG, Mowo, Pitture e Verniei Vol. 5, 2000, pages 61-67, and, in one embodiment, the polyurethanes with alkoxysilane groups from OSI-WITCO-GE.

As polyorganosiloxane compounds X and/or Y, non-limiting mention may be made of the resins of type MQ or MT, which themselves bear alkoxysilane and/or silanol end groups, for example, the poly(isobutylsilsesquioxane) resins functionalized by silanol groups sold under the designation SST-S7C41 (3 Si—OH groups) by the company Gelest.

2a. Additional Reactive Compounds

The composition according to the present disclosure can additionally comprise an additional reactive compound having at least two alkoxysilane or silanol groups.

For example, the composition can further comprise one or more organic or mineral particles with alkoxysilane and/or silanol groups on their surface, for example fillers surface-treated with said groups.

2b. Catalyst

The condensation reaction can be carried out in the presence of a metal-based catalyst, which can be present in the composition according to the disclosure. In one embodiment, the catalyst for use in this type of reaction is a titanium-based catalyst.

In another embodiment, the catalyst for use in the condensation is based on tetraalkoxytitanium of formula:

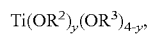

$Ti(OR^2)_y(OR^3)_{4-y}$, wherein each $R^2$ is chosen from tertiary alkyl radicals such as tert-butyl, tert-amyl and 2,4-dimethyl-3-pentyl; $R^3$ is an alkyl radical having from 1 to 6 carbon atoms, for example, a methyl, ethyl, n-propyl, isopropyl, n-butyl, sec-butyl, or hexyl group and y is a number in the range from 3 to 4, for example, from 3.4 to 4.

The catalyst can be present in the composition according to the present disclosure in an amount ranging from 0.0001 wt. % to 20 wt. %, relative to the total weight of the composition.

2c. Diluent

The composition according to the present disclosure can additionally comprise a volatile silicone oil (or diluent) for reducing the viscosity of the composition. In one embodiment, this oil can be chosen from linear short-chain silicones such as hexamethyldisiloxane, octamethyltrisiloxane, cyclic silicones such as octamethylcyclotetrasiloxane, and decamethylcyclopentasiloxane, or mixtures thereof.

This silicone oil can be present in the composition in an amount ranging from 5 to 95 wt. %, for example, from 10 to 80 wt. %, relative to the weight of the composition.

Some examples of a combination of compound X and Y having alkoxysilane groups and reacting by condensation, are the combination of the following mixtures A' and B' prepared by the company Dow Corning:

Mixture A':

| Ingredient (INCI Name) | CAS No. | Content (wt. %) | Function |
|---|---|---|---|
| Bis-Trimethoxysiloxyethyl Tetramethyldisiloxyethyl Dimethicone | PMN87176 | 25-45 | Polymer |
| Silica Silylate | 68909-20-6 | 5-20 | Filler |
| Disiloxane | 107-46-0 | 30-70 | Solvent |

Mixture B':

| Ingredient (INCI Name) | CAS No. | Content (wt. %) | Function |
|---|---|---|---|
| Disiloxane | 107-46-0 | 80-99 | Solvent |
| Tetra T Butyl Titanate | — | 1-20 | Catalyst |

It should also be noted that identical compounds X and Y are combined in mixture A'.

3. Crosslinking in the Presence of Peroxide

In at least one embodiment, this crosslinking reaction is carried out by heating at a temperature greater than or equal to 50° C., for example, greater than or equal to 80° C., and further, for example, at a temperature as high as 120° C.

When compounds X and Y react by cross-linking as described, compounds X and Y, which may be identical or different, may comprise at least two side groups —$CH_3$ and/or at least two side chains bearing a group —$CH_3$.

In at least one embodiment, compound X and Y are silicone compounds and can be chosen from non-volatile linear polydimethylsiloxanes of high molecular weight, having a degree of polymerization greater than 6 and having at least two side groups —$CH_3$ attached to the silicon atom and/or at least two side chains bearing a group —$CH_3$. Some examples of these polymers are described in the Catalogue "Reactive Silicones" of the company Gelest Inc., Edition 2004, page 6, and the copolymers (also called gums) of vinylmethylsiloxane-dimethylsiloxane having a molecular weight in the range from 500 000 to 900 000 and with a viscosity above 2 000 000 cSt.

In some embodiments, peroxides that can be used in the crosslinking reaction are benzoyl peroxide, and 2,4-dichlorobenzoyl peroxide, or mixtures thereof.

According to one embodiment, the hydrosilylation reaction or the condensation reaction or alternatively the crosslinking reaction in the presence of a peroxide between compounds X and Y is accelerated by supplying heat, for example raising the temperature of the system from 25° C. to 180° C. The system will react, in at least one embodiment, on keratin fibers.

In general, regardless of the type of reaction by which compound X and Y react together, the molar percentage of X relative to the total of compounds X and Y, is, for example, in the ratio X/(X+Y)×100, and can vary from 5% to 95%, from 10% to 90%, or from 20% to 80%.

Furthermore, the molar percentage of Y relative to the total of compounds X and Y, is, for example, the ratio Y/(X+Y)×100, and can vary from 5% to 95%, from 10% to 90%, or from 20% to 80%.

In at least one embodiment, compound X can have a weight-average molecular weight (Mw) in the range from 150 to 1 000 000, for example, from 200 to 800 000, or, for example from 200 to 250 000.

In at least one embodiment, compound Y can have a weight-average molecular weight (Mw) in the range from 200 to 1 000 000, for example, from 300 to 800 000, or, for example, from 500 to 250 000.

Compound X can be present in the composition in an amount ranging from 0.5% to 95 wt. % relative to the total weight of the composition, for example from 1% to 90% or, for example, from 5% to 80%.

Compound Y can be present in the composition in an amount ranging from 0.05% to 95 wt. % relative to the total weight of the composition, for example, from 0.1% to 90%, or, for example, from 0.2% to 80%.

The ratio of compound X to compound Y can be varied in such a way as to adjust the reaction rate and therefore the rate of film formation or so as to adapt the properties of the film formed (for example its adhesive properties) according to the intended application.

In at least one embodiment, compounds X and Y can be present at a molar ratio X/Y in the range from 0.05 to 20, for example, from 0.1 to 10.

In at least one embodiment, the composition according to the disclosure can additionally comprise at least one filler. For example, these fillers can be colloidal calcium carbonate, which may or may not be treated with stearic acid or stearate, silica such as fumed silicas, precipitated silicas, silicas treated to make them hydrophobic, ground quartz, alumina, aluminium hydroxide, titanium dioxide, diatomaceous earth, iron oxide, carbon black, and graphite. In one embodiment, the fillers are chosen from synthetic silicas in which the surface is modified with silicone compounds to make them hydrophobic at the surface. These fillers differ from one another in their surface properties, silicone compounds used for treating the silica, and manner in which the surface treatment is carried out. Said fillers make it possible to reduce the viscosity of the formulation obtained from compounds X and/or Y. Moreover, reinforcing fillers based on resin can also be used. In some embodiments, the fillers are silica, calcium carbonate, or resin-based fillers. Some examples of these fillers are the treated fillers Cab-O—Sil@TS-530, Aerosil@R8200, and Wacker HDX H2000.

Hydrophobic Direct Dyes

Within the scope of the disclosure, the hydrophobic dye is defined by the value of log P. This value of log P is conventionally the partition coefficient of the dye between octanol and water. The value of log P can be calculated by the method described in the article of Meylan and Howard "*Atom/Fragment contribution method for estimating octanol-water partition coefficient*", J. Pharm. Sci. 84: 83-92, 1995. This value can also be calculated with various commercially available software packages, which determine the value of log P in relation to the structure of a molecule. Some examples of software packages are Epiwinn Version 3.11 software from the Environment Agency of the United States, which has been used within the scope of the present disclosure.

The direct dyes that can be used in the composition of the present disclosure are hydrophobic dyes known by one skilled in the art, which have a log P greater than 2.

In at least one embodiment, the direct dyes that can be used according to the disclosure are chosen from neutral, acid or cationic nitro benzene direct dyes; neutral, acid or cationic azo direct dyes; quinone direct dyes, such as neutral, acid or cationic anthraquinone direct dyes; azine direct dyes; triarylmethane direct dyes; indoamino direct dyes, and natural direct dyes.

In at least one embodiment, the hydrophobic dyes are chosen so as to be dissolved or dispersed in the composition. In one embodiment, the hydrophobic dyes are dissolved in the composition. In another embodiment of the disclosure, the hydrophobic direct dye or dyes are soluble in the composition to at least 0.5 gram per liter, for example, to at least 1 gram per liter at a temperature of 25° C.

Examples of hydrophobic direct dyes include:

| Dye | Chemical structure | log P |
|---|---|---|
| Solvent Black 3 | 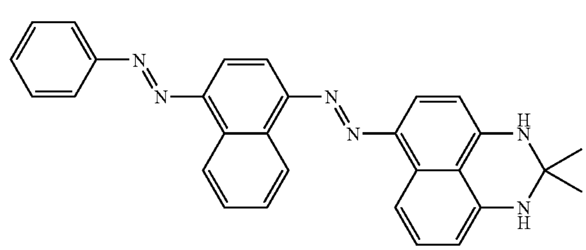 | 8.81 |

-continued
| Dye | Chemical structure | log P |
|---|---|---|
| Solvent Blue 104 | 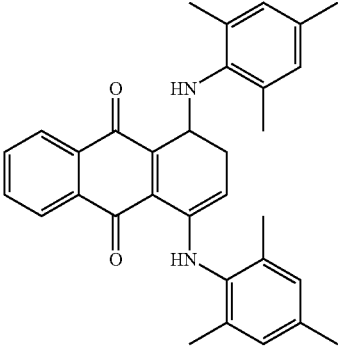 | 8.26 |
| Disperse Blue 134 | 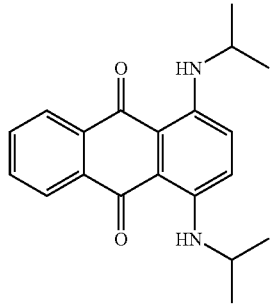 | 6.07 |
| Solvent Blue 14 | 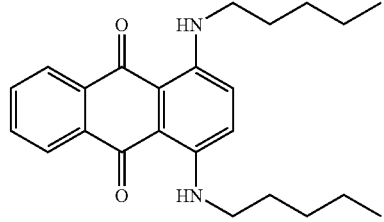 | 8.18 |
| Disperse Blue 14 | 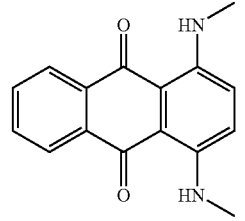 | 4.25 |
| Solvent Red 2 | 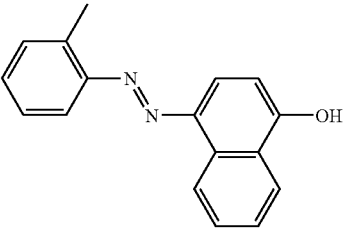 | 5.35 |

-continued

| Dye | Chemical structure | log P |
|---|---|---|
| Solvent Brown 5 | 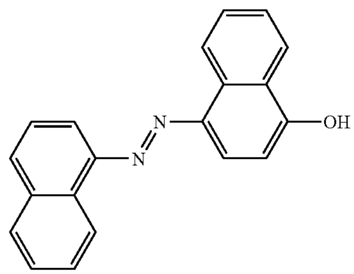 | 5.98 |
| Solvent Green 5 | 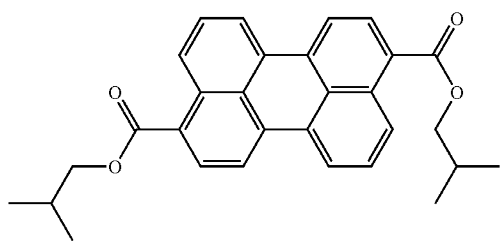 | 8.55 |
| Solvent Orange 2 | 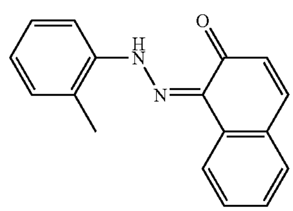 | 3.86 |
| Solvent Orange 1 | 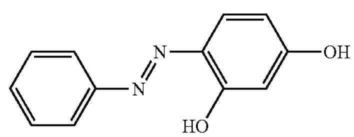 | 3.85 |
| Disperse Orange 24 | 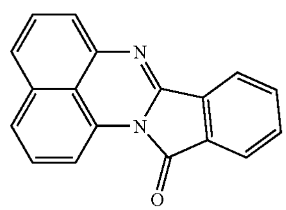 | 3.21 |
| Solvent Orange 63 | 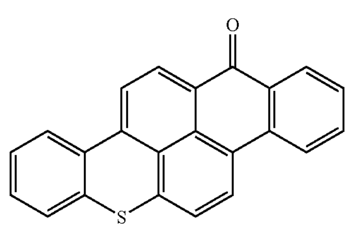 | 7.02 |
| Solvent Red 49 | 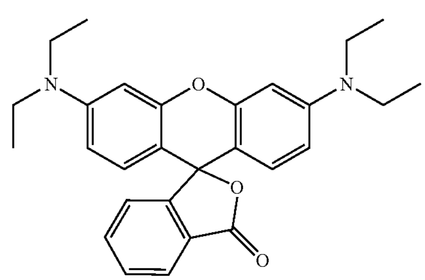 | 6.63 |

-continued
| Dye | Chemical structure | log P |
|---|---|---|
| Solvent Red 1 | 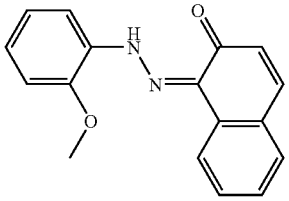 | 3.39 |
| Solvent Red 26 | 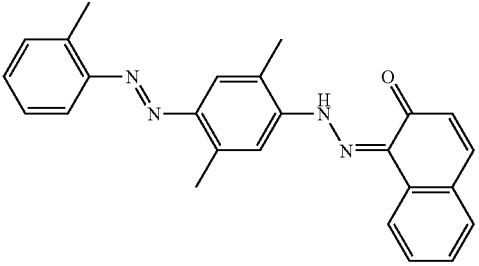 | 7.07 |
| Solvent Red 27 | 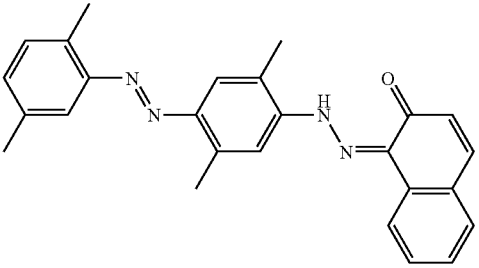 | 7.62 |
| Solvent Red 18 | 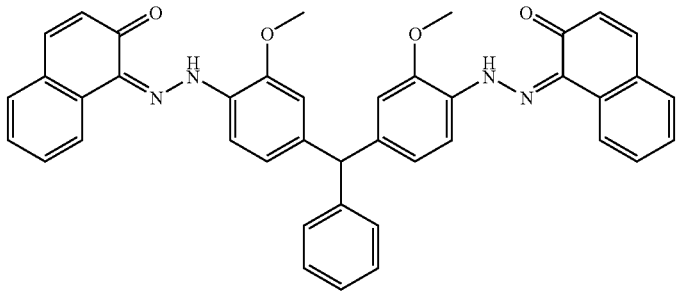 | 8.16 |
| Solvent Red 23 | 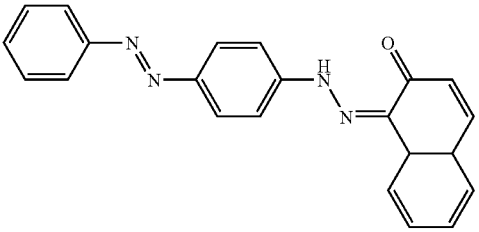 | 5.58 |

| Dye | Chemical structure | log P |
|---|---|---|
| Solvent Red 4 | 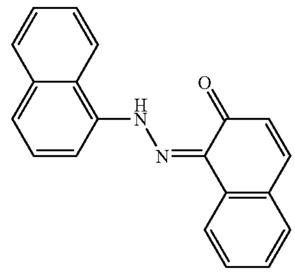 | 4.48 |
| Solvent Orange 7 | 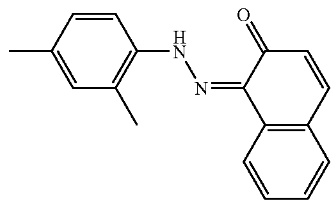 | 4.40 |
| Disperse Blue 72 | 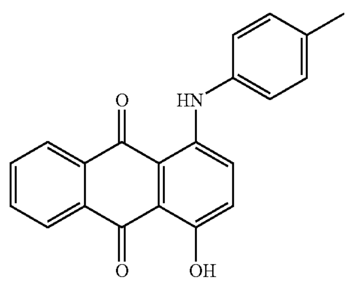 | 6.24 |
| Disperse Violet 26 | 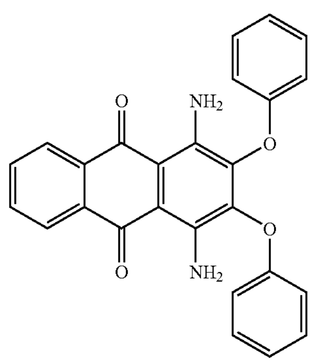 | 5.19 |
| Disperse Yellow 16 | 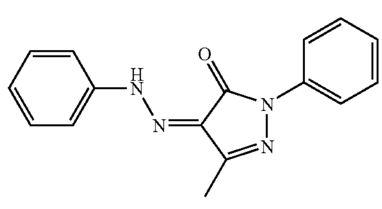 | 3.89 |
| Disperse Yellow 82 | 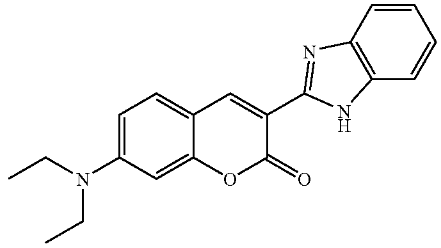 | 3.68 |

-continued
| Dye | Chemical structure | log P |
|---|---|---|
| Disperse Yellow 54 | 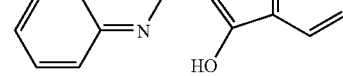 | 4.76 |
| Solvent Yellow 29 | 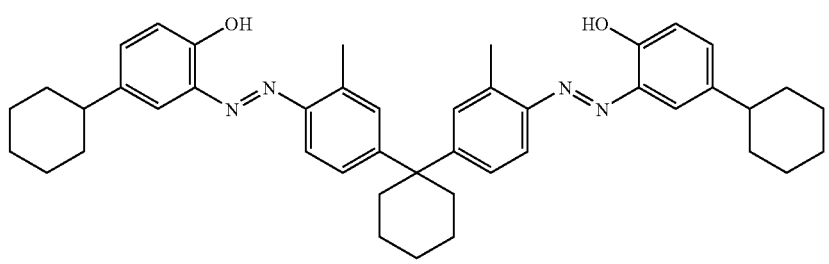 | 17.37 |
| Solvent Yellow 163 | 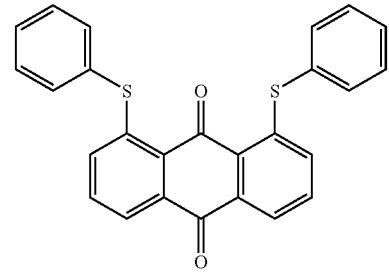 | 7.94 |
| Solvent Yellow 3 | 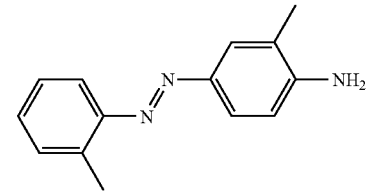 | 4.29 |
| Solvent Yellow 56 | 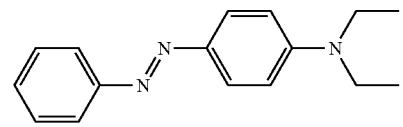 | 5.27 |
| Solvent Yellow 18 | 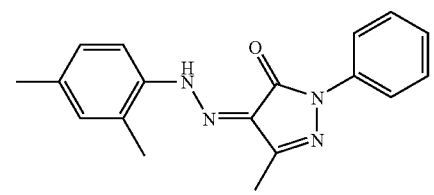 | 4.98 |
| Solvent Yellow 98 | 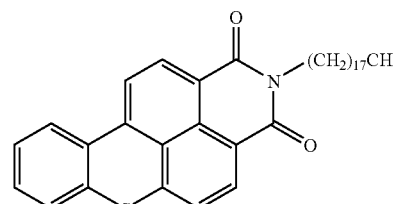 | 4.5 |

-continued
| Dye | Chemical structure | log P |
|---|---|---|
| Solvent Yellow 12 | 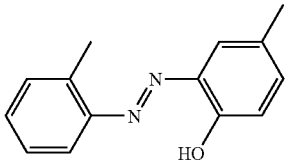 | 5.43 |
| Solvent Yellow 14 | 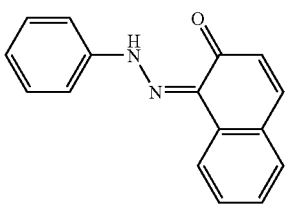 | 3.31 |
| Disperse Red 13 | 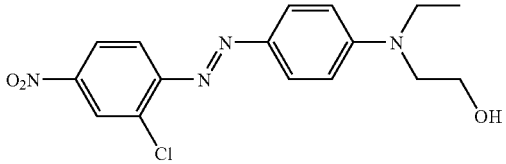 | 5.22 |
| Disperse Green 9 | 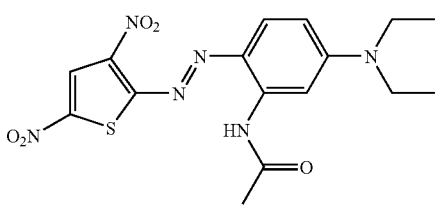 | 4.23 |
| Disperse Blue 148 | 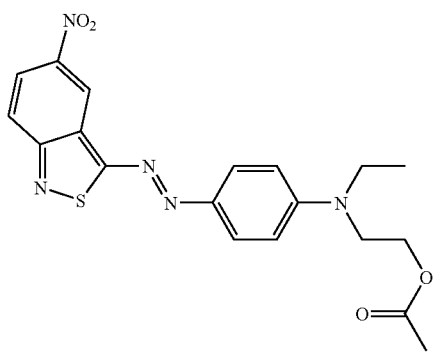 | 4.81 |
| Disperse Violet 63 | 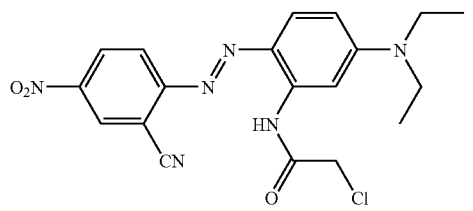 | 5.30 |
| Disperse Blue 60 | 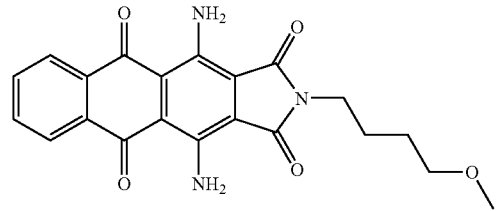 | 3.38 |

| Dye | Chemical structure | log P |
|---|---|---|
| Solvent Orange 15 | 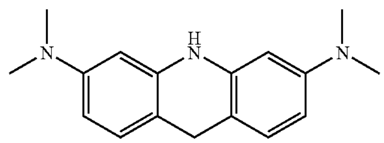 | 3.90 |

According to one embodiment, at least one of the hydrophobic direct dyes used within the scope of the disclosure has a log P greater than 4.

According to another embodiment, at least one of the hydrophobic direct dyes used within the scope of the disclosure has a log P greater than 6.

In embodiments of the present disclosure, the hydrophobic direct dye or dyes having a log P greater than 2 can be present in the composition in an amount ranging from 0.0001 to 10 wt. %, for example, from about 0.001 to 5 wt. %, relative to the total weight of the composition.

Organic Solvents

As used in the present disclosure, "organic solvent" means an organic substance that is liquid at a temperature of 25° C. and at atmospheric pressure (760 mm of Hg) and is able to dissolve another substance without altering it chemically.

In some embodiments, the organic solvent or solvents used within the scope of the disclosure are different from the compounds X and Y used within the scope of the disclosure.

In some embodiments, the organic solvent or solvents used in the present disclosure are chosen from aromatic alcohols such as benzyl alcohol, phenoxyethanol, phenylethyl alcohol; liquid aliphatic alcohols, for example, $C_{10}$-$C_{30}$; $C_1$-$C_6$ alkanols such as ethanol, isopropanol, n-propanol, butanol, n-pentanol, 1,2-propanediol, 1,3-propanediol, 1-methoxy-2-propanol, 1-ethoxy-2-propanediol, 1,3 and 1,4-butanediol, 1,2-hexanediol; polyols and ethers of polyols possessing a free —OH functional group such as 2-butoxyethanol, propylene glycol, monomethylether of propylene glycol, monoethylether and monomethylether of diethylene glycol, ethyleneglycol monoethyl ether, ethyleneglycol monobutyl ether, neopentyl glycol, isoprene glycol, glycerol, glycol, dipropylene glycol, butylene glycol, butyl diglycol; volatile silicones such as short-chain linear silicones such as hexamethyldisiloxane and octamethyltrisiloxane, cyclic silicones such as octamethylcyclotetrasiloxane, decamethylcyclopentasiloxane, dodecamethylcyclohexasiloxane, polydimethylsiloxanes whether or not modified with alkyl and/or amine and/or imine and/or fluoroalkyl and/or carboxylic and/or betaine and/or quaternary ammonium functional groups; modified liquid polydimethylsiloxanes; mineral, organic or vegetable oils; alkanes, for example, linear or branched $C_5$ to $C_{20}$ alkanes; liquid fatty acids; and liquid aliphatic esters, for example, liquid benzoates or salicylates of aliphatic alcohols.

In other embodiments, the organic solvent or solvents are chosen from organic oils; silicones such as volatile silicones, gums or oils of silicones, aminated or not, and mixtures thereof; mineral oils; vegetable oils such as olive oil, castor oil, colza oil, copra oil, wheat germ oil, sweet almond oil, avocado oil, macadamia oil, apricot oil, safflower oil, candlenut oil, wild flax oil, tamanu oil, lemon oil or organic compounds such as linear or branched $C_5$-$C_{20}$ alkanes such as isododecane, isohexadecane, isoparaffinic compounds such as the products marketed under the name Isopar E, acetone, methyl ethyl ketone, liquid esters of $C_1$-$C_{20}$ acids and esters of $C_1$-$C_8$ alcohols such as methyl acetate, butyl acetate, ethyl acetate and isopropyl myristate, dimethoxyethane, diethoxyethane, liquid $C_{10}$-$C_{30}$ aliphatic alcohols such as oleic alcohol, esters of fatty alcohols or of liquid fatty acids such as benzoates of $C_{10}$-$C_{30}$ fatty alcohols and mixtures thereof; isononyl isononanoate, isostearyl malate, pentaerythrityl tetra-isostearate, tridecyl trimelate; polybutene oil; cyclopentasiloxane (14.7 wt. %)/polydimethylsiloxane mixture dihydroxylated in positions α and ω (85.3 wt. %), and mixtures thereof.

According to at least one embodiment, the at least one organic solvent is chosen from silicones such as liquid polydimethylsiloxanes and modified liquid polydimethylsiloxanes, the viscosity at 25° C. being from 0.1 cSt to 1 000 000 cSt, and for example, from 1 cSt to 30 000 cSt.

In at least one embodiment, the oils may be chosen from:

the mixture of alpha-omega-dihydroxylated polydimethylsiloxane/cyclopentadimethylsiloxane (14.7/85.3) marketed by Dow Corning under the name DC 1501 Fluid;

the mixture of alpha-omega-dihydroxylated polydimethylsiloxane/polydimethylsiloxane marketed by Dow Corning under the name DC 1503 Fluid;

the mixture of dimethicone/cyclopentadimethylsiloxane marketed by Dow Corning under the name DC 1411 Fluid or that marketed by Bayer under the name SF1214;

the cyclopentadimethylsiloxane marketed by Dow Corning under the name DC245 Fluid;

and the respective mixtures of these oils.

These organic solvents can be used as diluent for the polycondensation reactions.

The at least one organic solvent is present in the composition in an amount ranging from 0.01 to 99 wt. %, for example, from 50 to 99 wt. %, relative to the total weight of the composition.

The composition of the disclosure can contain, in addition to the at least one organic solvent, water in an amount ranging from 1 to 99%, and for example, from 1 to 50%, relative to the total weight of the composition. In other embodiments of the present disclosure, the composition can be anhydrous, i.e., containing less than 1 wt. % water relative to the total weight of the composition.

In at least one embodiment of the present disclosure, the composition of can be in the form of an emulsion and/or can be encapsulated. When the composition is an emulsion, it is for example constituted of a dispersed or continuous phase which can be water, $C_1$-$C_4$ aliphatic alcohols, or mixtures thereof, and an organic phase that is insoluble in water.

In some embodiments, the composition according to the disclosure can also contain, in addition to compounds X and Y of the disclosure, the hydrophobic dyes and any organic solvents, at least one agent usually employed in cosmetics, chosen from reducing agents, fats, plasticizers, softeners, antifoaming agents, moisturizing agents, pigments, clays, mineral fillers, UV filters, mineral colloids, peptizing agents, perfumes, preservatives, anionic, cationic, nonionic or amphoteric surfactants, fixative or non-fixative polymers, proteins, vitamins, direct dyes other than the hydrophobic dyes of the disclosure, oxidative dyes, lustre agents, propellants, and mineral or organic thickeners such as benzylidene-sorbitol and N-acylamino acids, waxes whether oxyethylenated or not, paraffins, solid $C_{10}$-$C_{30}$ fatty acids such as stearic acid, lauric acid, $C_{10}$-$C_{30}$ aliphatic amides such as lauric diethanolamide, and solid esters of aliphatic alcohols or of fatty acids.

In some embodiments, the presently disclosed composition can be in various forms, such as lotions, sprays, mousses and can be applied in the form of shampoo or after-shampoo product.

In embodiments in which the composition is in the form of a spray, the composition of the disclosure can contain a propellant. The propellant comprises, for example, the compressed or liquefied gases usually employed for the preparation of aerosols. Air, carbon dioxide, compressed nitrogen or alternatively a soluble gas such as dimethyl ether, halogenated hydrocarbons (especially fluorinated) or non-halogenated hydrocarbons (butane, propane, isobutane) and mixtures thereof, may be used.

It is also possible, if required, to use aerosols with pocket(s), containing one or more pockets.

The present disclosure further relates to a method for the coloration of keratin fibers comprising applying to the keratin fibers a composition comprising:
  a cosmetically acceptable medium;
  at least one compound X and at least one compound Y, wherein at least one of the compounds X and Y is a silicone compound, and wherein X and Y, when brought in contact with each other, react together via
    a hydrosilylation reaction,
    a condensation reaction, or
    a crosslinking reaction in the presence of at least one peroxide;
  at least one hydrophobic direct dye having a log P greater than 2; and
  optionally at least one organic solvent.

The at least one compound X, the at least one compound Y, the at least one hydrophobic direct dye and the at least one organic solvent, if present, have the same definitions as above.

In at least one embodiment, the at least one compound X, the at least one compound Y, the at least one hydrophobic direct dye and the at least one organic solvent, if present, can be applied to the keratin fibers from several compositions containing the at least one compound X, the at least one compound Y, the at least one hydrophobic direct dye and the at least one organic solvent if present, alone or mixed, or from a single composition containing the at least one compound X, the at least one compound Y, the at least one hydrophobic direct dye and the at least one organic solvent, if present.

According to one embodiment of the disclosure, a composition (A) comprising the at least one compound X, the at least one compound Y, the at least one hydrophobic direct dye, and the at least one organic solvent, if present, is applied to the keratin fibers.

According to another embodiment of the disclosure, the following are applied to the keratin fibers: a composition (B) comprising the at least one hydrophobic direct dye, and a composition (C) comprising the at least one compound X and the at least one compound Y, the at least one organic solvent, if any, being contained in composition (B) and/or composition (C), and compositions (B) and (C) can be applied in any order.

According to another embodiment of the disclosure, the following are applied to the keratin fibers: a composition (B) comprising the at least one hydrophobic direct dye, a composition (D) comprising the at least one compound X and a composition (E) comprising the at least one compound Y, the at least one organic solvent, if any, being contained in composition (B) and/or composition (D) and/or composition (E), and compositions (B), (D) and (E) can be applied in any order.

According to another embodiment of the disclosure, the following are applied to the keratin fibers: a composition (F) comprising the at least one compound X and the at least one hydrophobic direct dye and a composition (E) comprising the at least one compound Y, the at least one organic solvent, if any, being contained in composition (F) and/or composition (E), and compositions (F) and (E) can be applied in any order.

According to another embodiment of the disclosure, the following are applied on the keratin fibers: a composition (D) comprising the at least one compound X and a composition (G) comprising the at least one compound Y and the at least one hydrophobic direct dye, the at least one organic solvent, if any, being contained in composition (D) and/or composition (G), and compositions (D) and (G) can be applied in any order.

According to one embodiment of the disclosure, the composition comprising the at least one hydrophobic direct dye is applied before the composition or compositions comprising at least one compound X and/or at least one compound Y.

In at least one embodiment, when compounds X and Y react with each other by a crosslinking reaction, at least one peroxide as defined above is applied to the keratin fibers.

The at least one peroxide can be present in any one of the compositions, or in more than one of the compositions applied on the keratin fibers already mentioned, or in a supplementary composition, in which case various compositions can be applied to the keratin fibers in any order.

According to one embodiment of the disclosure, at least one catalyst as defined above is applied to the keratin fibers in order to activate the reaction between compound or compounds X and compound or compounds Y.

For example, the at least one catalyst can be present in any one or more of the compositions applied on the keratin fibers already mentioned or in a supplementary composition, and the various compositions can be applied to the keratin fibers in any order.

In at least one embodiment, the catalysts chosen are those that are described above.

In embodiments when at least one catalyst and/or at least one peroxide are applied to the keratin fibers, the at least one compound X, the at least one compound Y, the at least one catalyst and/or the at least one peroxide are not present simultaneously in the same composition. On the contrary, they can be mixed at the moment of use.

According to another embodiment of the disclosure, at least one additional reactive compound as defined above is applied to the keratin fibers.

For example, the at least one additional reactive compound can be present in any one of the compositions, or in more than one of the compositions applied to the keratin fibers already mentioned, or in a supplementary composition, and the various compositions can be applied to the keratin fibers in any order.

The various compositions employed in the method according to the disclosure can be applied on dry or on wet hair. Intermediate drying and/or rinsing can be carried out between each application.

Each composition that can be used in the method according to the disclosure can additionally contain various conventional cosmetic additives as defined above.

In some embodiments, each composition that can be used in the method according to the disclosure comprises a cosmetically acceptable medium, which carries the at least one compound X and/or the at least one compound Y, and is chosen in such a way that compounds X and Y are able to react with one another by a reaction of hydrosilylation, of condensation, or of crosslinking in the presence of peroxide, after application of the cosmetic composition to the hair.

The deposit thus formed may have, advantageously, a low expected solubility. Moreover, it may possess good affinity for the surface of the keratin fibers, which guarantees better lasting qualities of all of the deposit.

When compounds X and Y are applied to the hair separately, the layered compositions deposited can also be advantageous for preserving the cosmetic or optical properties of the compound constituting the upper portion of the deposit.

Employing the same methods, it is possible to effect multiple superpositions of layers of compounds X and Y, alternating or not, to achieve the type of deposit on the hair that is desired (in terms of chemical nature, mechanical resistance, thickness, appearance, feel, etc.).

The present disclosure further relates to a kit for dyeing keratin fibers comprising at least two compositions packaged separately, the kit comprising:

at least one compound X and at least one compound Y, wherein at least one of the compounds X and Y is a silicone compound, and wherein, when placed in contact with each other, said compounds X and Y react with each other by a hydrosilylation reaction, a condensation reaction, or a crosslinking reaction in the presence of peroxide;

at least one hydrophobic direct dye whose logP is greater than 2; and optionally at least one organic solvent.

In the kit, the at least one compound X, the at least one compound Y, the at least one hydrophobic direct dye and the at least one organic solvent, if present, are defined as above.

According to one embodiment of the disclosure, a first compartment comprises composition (B) as defined above and a second compartment comprises composition (C) as defined above.

According to another embodiment, a first compartment comprises composition (B) as defined above, a second compartment comprises composition (D) as defined above and a third compartment comprises composition (E) as defined above.

According to another embodiment of the disclosure, a first compartment comprises composition (F) as defined above and a second compartment comprises composition (E) as defined above.

According to another embodiment, a first compartment comprises composition (D) as defined above and a second compartment comprises composition (G) as defined above.

In at least one embodiment, when compounds X and Y react with each other by a crosslinking reaction, all of the compositions may additionally include at least one peroxide as defined above.

For example, one or more of the compositions contained in the kit can additionally include at least one peroxide.

The kit can also contain a supplementary composition comprising at least one peroxide, in a cosmetically acceptable medium.

According to one embodiment of the disclosure, all said compositions additionally include at least one catalyst as defined above, i.e., one or more of the compositions contained in the kit include at least one catalyst or the kit contains a supplementary composition comprising, in a cosmetically acceptable medium, at least one catalyst.

When all said compositions include at least one catalyst and/or at least one peroxide, the at least one compound X, the at least one compound Y, the at least one catalyst and/or the at least one peroxide may not be present simultaneously in the same composition. On the contrary, they can be mixed at the moment of use.

The present disclosure also relates to a process for coloring of keratin fibers to obtain a coloration resistant to shampoos, comprising applying to said keratin fibers a composition comprising:

at least one compound X and at least one compound Y, wherein at least one of the compounds X and Y is a silicone compound, wherein, when X and Y are placed in contact with each other they react together via a hydrosilylation reaction, a condensation reaction, or a crosslinking reaction in the presence of at least one peroxide;

at least one hydrophobic direct dye having a log P greater than 2; and optionally at least one organic solvent.

The at least one compound X, the at least one compound Y, the at least one hydrophobic direct dye and the at least one organic solvent, if present, being as defined above. The coloration of the keratin fibers is resistant to shampoos.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

In the example of a composition described below, the following combination of mixtures A' and B' produced by the company Dow Corning was used:

Mixture A':

| Ingredient (INCI Name) | CAS No. | Content (wt. %) | Function |
|---|---|---|---|
| Bis-Trimethoxysiloxyethyl Tetramethyldisiloxyethyl Dimethicone | PMN87176 | 25-45 | Polymer |
| Silica Silylate | 68909-20-6 | 5-20 | Filler |
| Disiloxane | 107-46-0 | 30-70 | Solvent |

Mixture B':

| Ingredient (INCI Name) | CAS No. | Content (wt. %) | Function |
|---|---|---|---|
| Disiloxane | 107-46-0 | 80-99 | Solvent |
| Tetra T Butyl Titanate | — | 1-20 | Catalyst |

It should also be noted that identical compounds X and Y were combined in mixture A'.

Example 1

Compositions 1 and 2 as defined below were prepared:

| | in g |
|---|---|
| Composition 1 | |
| Cyclopentadimethylsiloxane marketed by Dow Corning under the name DC245 Fluid | 82.34 |
| Mixture A' | 15.15 |
| Solvent Blue 14 (log P = 8.18) | 1 |
| Composition 2 | |
| Mixture B' | 1.51 |

Compositions 1 and 2 were mixed before use, to obtain 100 g of a combination composition. 0.5 g of this composition was applied on a lock of 1 g of clean and wet, natural grey hair with 90% white hair. After waiting one hour, the lock of hair was dried with a hair dryer for 2 minutes. A colored lock was obtained in which the hair was coated and had increased body. The coloration was resistant to shampoos.

In the example of a composition described below, the following combination of mixtures A and B produced by the company Dow Corning was used:

Mixture A:

| Ingredient (INCI Name) | CAS No. | Content (wt. %) | Function |
|---|---|---|---|
| Dimethyl Siloxane, Dimethylvinylsiloxy-terminated | 68083-19-2 | 55-95 | Polymer |
| Silica Silylate | 68909-20-6 | 10-40 | Filler |
| 1,3-Diethenyl-1,1,3,3-Tetramethyldisiloxane complexes | 68478-92-2 | Trace | Catalyst |
| Tetramethyldivinyldisiloxane | 2627-95-4 | 0.1-1 | Polymer |

Mixture B:

| Ingredient (INCI Name) | CAS No. | Content (wt. %) | Function |
|---|---|---|---|
| Dimethyl Siloxane, Dimethylvinylsiloxy-terminated | 68083-19-2 | 55-95 | Polymer |
| Silica Silylate | 68909-20-6 | 10-40 | Filler |
| Dimethyl, Methylhydrogen Siloxane, trimethylsiloxy-terminated | 68037-59-2 | 1-10 | Polymer |

Example 2

Compositions 3 and 4 as defined below were prepared:

| | wt. % |
|---|---|
| Composition 3 | |
| Cyclopentadimethylsiloxane marketed by Dow Corning under the name DC245 Fluid | 88 |
| Mixture A | 10 |
| Solvent Blue 14 (log P = 8.18) | 2 |
| Composition 4 | |
| Cyclopentadimethylsiloxane marketed by Dow Corning under the name DC245 Fluid | 90 |
| Mixture B | 10 |

Compositions 3 and 4 were mixed before use, in the weight ratio 50/50. 0.5 g of this mixture was applied on a lock of 1 g of clean and wet, natural grey hair with 90% white hair. After waiting one hour, the lock of hair was dried with a hair dryer for 2 minutes. A colored lock was obtained in which the hair was coated and had increased body. The coloration was resistant to shampoos.

What is claimed is:

1. A composition for coloring keratin fibers comprising:
   a cosmetically acceptable medium;
   at least one compound X of polyorganosiloxane comprising siloxane units of a formula:

$$R_m R' SiO_{\frac{(3-m)}{2}} \quad (I)$$

in which:
   R is a linear or cyclic, monovalent hydrocarbon group having from 1 to 30 atoms;
   m is 1 or 2; and
   R' is chosen from an unsaturated aliphatic hydrocarbon group having from 2 to 10 carbon atoms and an unsaturated cyclic hydrocarbon group having from 5 to 8 carbon atoms;
   at least one compound Y of an organosiloxane comprising at least one alkylhydrogensiloxane unit of the following formula:

$$R_p HSiO_{\frac{(3-p)}{2}} \quad (III)$$

wherein:
   R is chosen from a linear or cyclic, monovalent hydrocarbon group having from 1 to 30 carbon atoms and a phenyl group; and
   p is 1 or 2;
   wherein, when compounds X and Y are placed in contact with each other they react together by a hydrosilyation reaction;
   at least one hydrophobic direct dye of anthraquinone dyes having a log P greater than 2; and
   optionally at least one organic solvent.

2. The composition according to claim 1, further comprising at least one catalyst.

3. The composition according to claim 1, wherein R' is chosen from a vinyl group and a —R"—CH═CHR'" group in which R" is a divalent aliphatic hydrocarbon chain having from 1 to 8 carbon atoms, joined to the silicon atom, and R'" is chosen from a hydrogen atom and an alkyl radical having from 1 to 4 carbon atoms.

4. The composition according to claim 1, wherein R is chosen from an alkyl radical having from 1 to 10 carbon and a phenyl group and R' is a vinyl group.

5. The composition according to claim 4, wherein the at least one compound X further comprises units of formula $$R_m R' SiO_{\frac{(3-m)}{2}} \qquad (I)$$

wherein R is linear or cyclic, monovalent hydrocarbon group having from 1 to 30 carbon atoms, and n is 1, 2 or 3.

6. The composition according to claim 1, wherein R is a $C_1$-$C_{10}$ alkyl group.

7. The composition according to claim 2, wherein the at least one catalyst is chosen from platinum-based and tin-based catalysts.

8. The composition according to claim 7, wherein the at least one catalyst is present in the composition in an amount ranging from 0.0001 to 20 wt. % relative to the total weight of the composition.

9. The composition according to claim 1, wherein the at least one compound X is a polydimethylsiloxane with vinylic end groups and the at least one compound Y is methylhydrogenosiloxane.

10. The composition according to claim 1, further comprising at least one filler chosen from silica and surface-treated silica.

11. The composition according to claim 1, wherein the at least one compound X has a weight-average molecular weight (Mw) in the range from 150 to 1 000 000.

12. The composition according to claim 1, wherein the at least one compound Y has a weight-average molecular weight (Mw) in the range from 200 to 1 000 000.

13. The composition according to claim 1, wherein the at least one hydrophobic direct dye is chosen from one of:

| Dye | Chemical structure | log P |
|---|---|---|
| Solvent Black 3 | 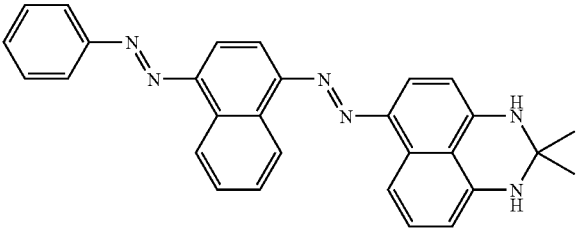 | 8.81 |
| Solvent Blue 104 | 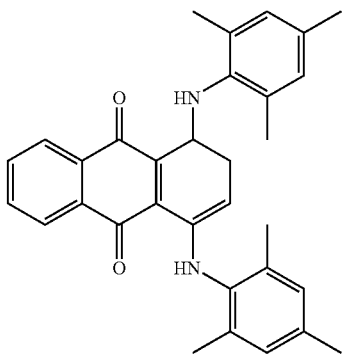 | 8.26 |
| Disperse Blue 134 | 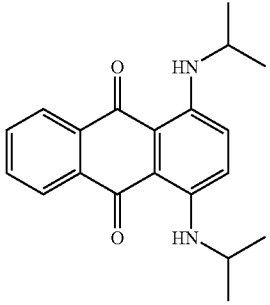 | 6.07 |

-continued

| Dye | Chemical structure | log P |
|---|---|---|
| Solvent Blue 14 | 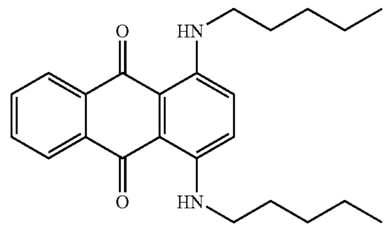 | 8.18 |
| Disperse Blue 14 | 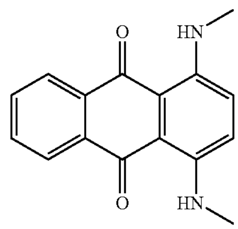 | 4.25 |
| Solvent Red 2 | 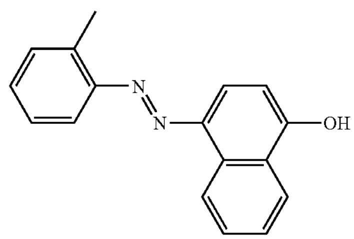 | 5.35 |
| Solvent Brown 5 | 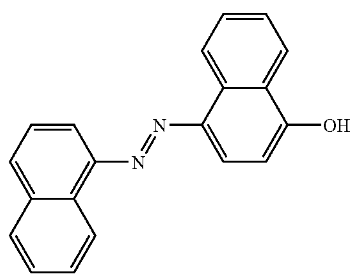 | 5.98 |
| Solvent Green 5 | 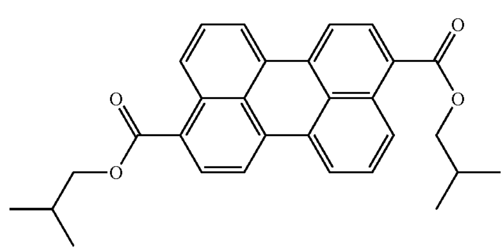 | 8.55 |
| Solvent Orange 2 | 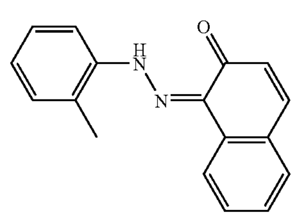 | 3.86 |
| Solvent Orange 1 | 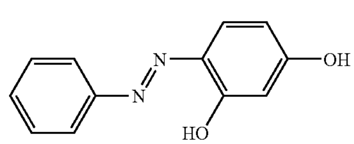 | 3.85 |

-continued

| Dye | Chemical structure | log P |
|---|---|---|
| Disperse Orange 24 | 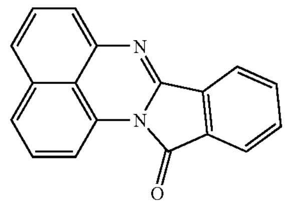 | 3.21 |
| Solvent Orange 63 | 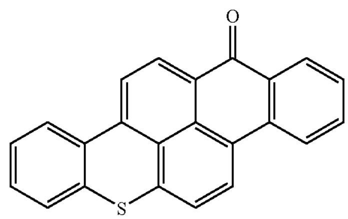 | 7.02 |
| Solvent Red 49 | 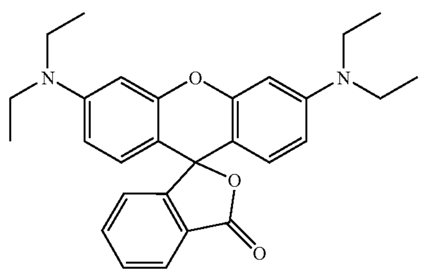 | 6.63 |
| Solvent Red 1 | 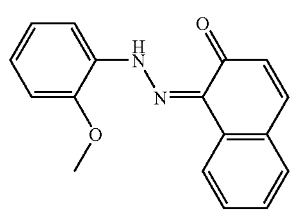 | 3.39 |
| Solvent Red 26 | 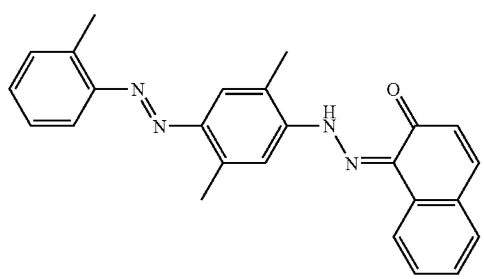 | 7.07 |
| Solvent Red 27 | 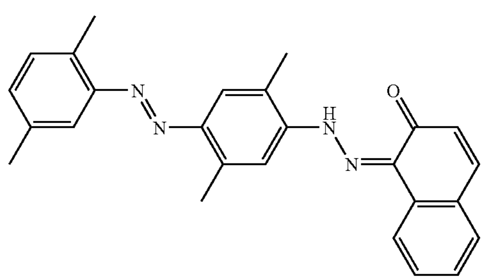 | 7.62 |

-continued

| Dye | Chemical structure | log P |
|---|---|---|
| Solvent Red 18 | 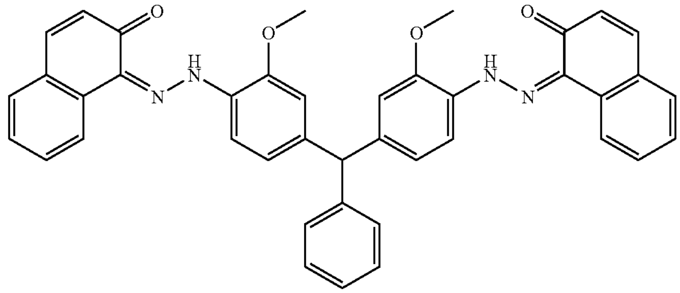 | 8.16 |
| Solvent Red 23 | 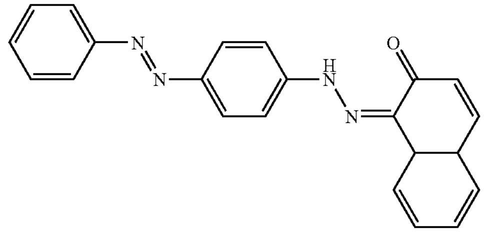 | 5.58 |
| Solvent Red 4 | 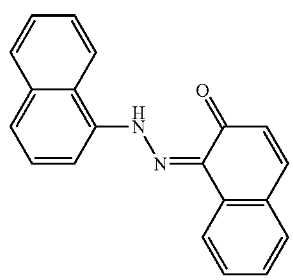 | 4.48 |
| Solvent Orange 7 | 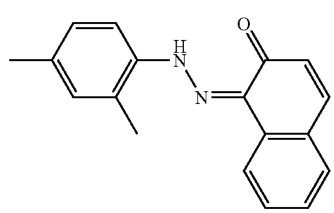 | 4.40 |
| Disperse Blue 72 | 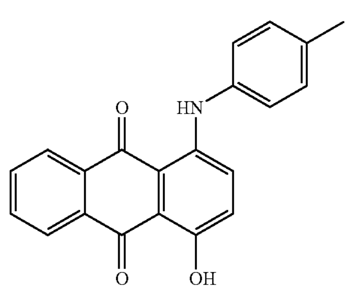 | 6.24 |

-continued

| Dye | Chemical structure | log P |
|---|---|---|
| Disperse Violet 26 | 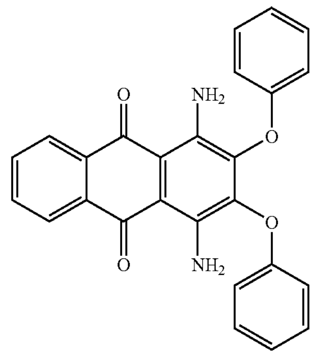 | 5.19 |
| Disperse Yellow 16 | 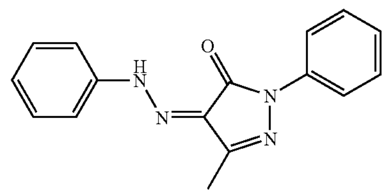 | 3.89 |
| Disperse Yellow 82 | 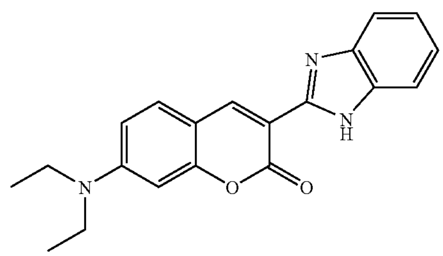 | 3.68 |
| Disperse Yellow 54 | 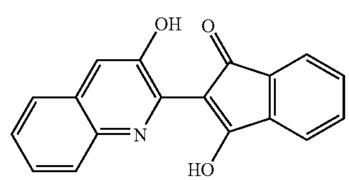 | 4.76 |
| Solvent Yellow 29 | 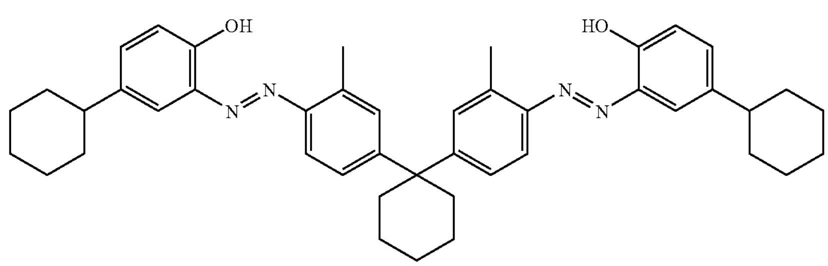 | 17.37 |
| Solvent Yellow 163 | 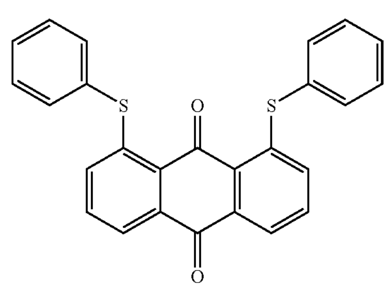 | 7.94 |

-continued

| Dye | Chemical structure | log P |
|---|---|---|
| Solvent Yellow 3 | 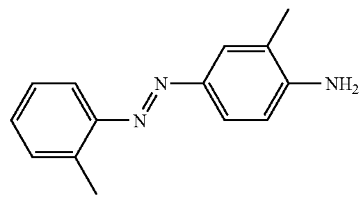 | 4.29 |
| Solvent Yellow 56 | 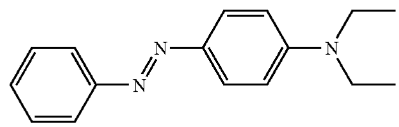 | 5.27 |
| Solvent Yellow 18 | 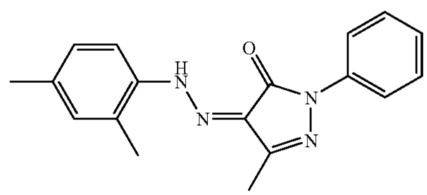 | 4.98 |
| Solvent Yellow 98 | 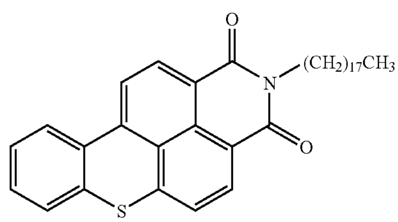 | 4.5 |
| Solvent Yellow 12 | 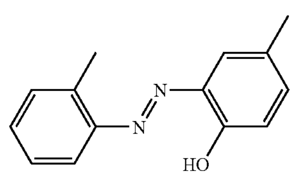 | 5.43 |
| Solvent Yellow 14 | 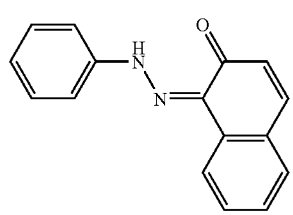 | 3.31 |
| Disperse Red 13 | 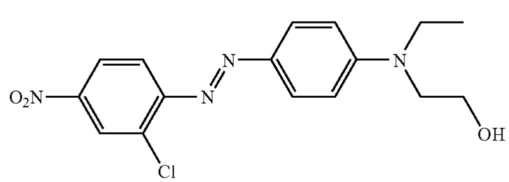 | 5.22 |
| Disperse Green 9 | 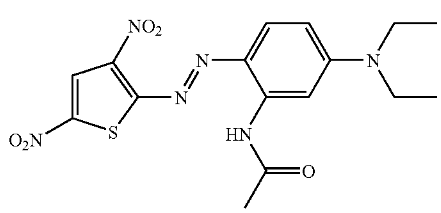 | 4.23 |

-continued

| Dye | Chemical structure | log P |
|---|---|---|
| Disperse Blue 148 | 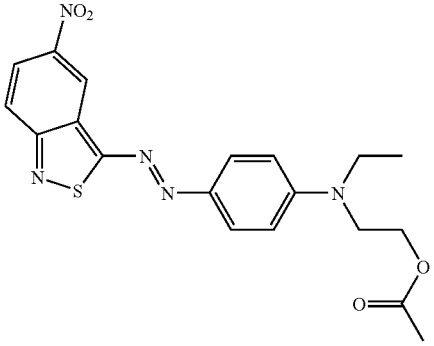 | 4.81 |
| Disperse Violet 63 | 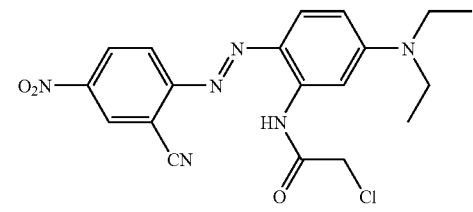 | 5.30 |
| Disperse Blue 60 | 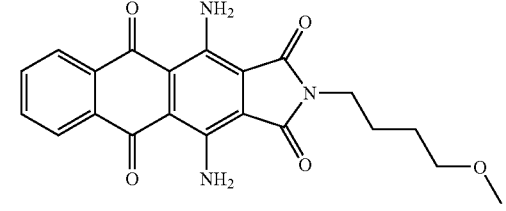 | 3.38 |
| Solvent Orange 15 | 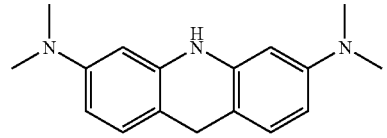 | 3.90. |

14. The composition according to claim 1, wherein the at least one hydrophobic direct dye is present in an amount from 0.0001 to 10%, relative to the total weight of the composition.

15. The composition according to claim 1, wherein the at least one organic solvent is chosen from organic oils; silicones; mineral oils; vegetable oils; $C_5$-$C_{20}$ alkanes; acetone; methyl ethyl ketone; liquid esters of $C_1$-$C_{20}$ acids and of $C_1$-$C_8$ alcohols; dimethoxyethane; diethoxyethane; liquid $C_{10}$-$C_{30}$ fatty alcohols; esters of fatty alcohols or of liquid fatty acids; isononyl isononanoate; isostearyl malate; pentaerythrityl tetra-isostearate; tridecyl trimelate; and polybutene oil; and mixtures thereof.

16. The composition according to claim 15, wherein the at least one organic solvent is chosen from silicones.

17. A method of coloring keratin fibers, comprising applying to said keratin fibers a composition comprising:
at least one cosmetically acceptable medium;
at least one compound X of polyorganosiloxane comprising siloxane units of a formula:

 (I)

in which:
R is a linear or cyclic, monovalent hydrocarbon group having from 1 to 30 atoms;

m is 1 or 2; and
R' is chosen from an unsaturated aliphatic hydrocarbon group having from 2 to 10 carbon atoms and an unsaturated cyclic hydrocarbon group having from 5 to 8 carbon atoms;
at least one compound Y of an organosiloxane comprising at least one alkylhydrogensiloxane unit of the following formula:

 (III)

wherein:
R is chosen from a linear or cyclic, monovalent hydrocarbon group having from 1 to 30 carbon atoms and a phenyl group; and
p is 1 or 2;
wherein, when compounds X and Y are placed in contact with each other they react together by a hydrosilyation reaction;
at least one hydrophobic direct dye of anthraquinone dyes having a log P greater than 2; and
optionally at least one organic solvent.

18. A kit for coloring keratin fiber, said kit comprising at least two compositions packaged separately, the kit comprising:

at least one compound X of polyorganosiloxane comprising siloxane units of a formula:

$$R_m R' SiO_{\frac{(3-m)}{2}} \quad (I)$$

in which:
R is a linear or cyclic, monovalent hydrocarbon group having from 1 to 30 atoms;
m is 1 or 2; and
R' is chosen from an unsaturated aliphatic hydrocarbon group having from 2 to 10 carbon atoms and an unsaturated cyclic hydrocarbon group having from 5 to 8 carbon atoms;

at least one compound Y of an organosiloxane comprising at least one alkylhydrogensiloxane unit of the following formula:

$$R_p HSiO_{\frac{(3-p)}{2}} \quad (III)$$

wherein:
R is chosen from a linear or cyclic, monovalent hydrocarbon group having from 1 to 30 carbon atoms and a phenyl group; and
p is 1 or 2;

wherein, when compounds X and Y are placed in contact with each other they react together by a hydrosilyation reaction;
at least one hydrophobic direct dye of anthraquinone dyes having a log P greater than 2; and
optionally at least one organic solvent.

19. A method of coloring keratin fibers to obtain a coloration resistant or substantially resistant to shampoos, comprising to said keratin fibers a composition comprising:
at least one cosmetically acceptable medium;
at least one compound X of polyorganosiloxane comprising siloxane units of a formula:

$$R_m R' SiO_{\frac{(3-m)}{2}} \quad (I)$$

in which:
R is a linear or cyclic, monovalent hydrocarbon group having from 1 to 30 atoms;
m is 1 or 2; and
R' is chosen from an unsaturated aliphatic hydrocarbon group having from 2 to 10 carbon atoms and an unsaturated cyclic hydrocarbon group having from 5 to 8 carbon atoms;

at least one compound Y of an organosiloxane comprising at least one alkylhydrogensiloxane unit of the following formula:

$$R_p HSiO_{\frac{(3-p)}{2}} \quad (III)$$

wherein:
R is chosen from a linear or cyclic, monovalent hydrocarbon group having from 1 to 30 carbon atoms and a phenyl group; and
p is 1 or 2;

wherein, when compounds X and Y are placed in contact with each other they react together by a hydrosilyation reaction;
at least one hydrophobic direct dye of anthraquinone dyes having a log P greater than 2; and
optionally at least one organic solvent;

wherein said ingredients are present in an amount effective to obtain a coloration that is resistant or substantially resistant to shampoos.

20. The composition according to claim 1, wherein the at least one hydrophobic direct dye has a log P greater than 4.

21. The composition according to claim 20, wherein the at least one hydrophobic direct dye has a log P greater than 6.

* * * * *

UNITED STATES PATENT AND TRADEMARK OFFICE
CERTIFICATE OF CORRECTION

| | | |
|---|---|---|
| PATENT NO. | : 7,780,742 B2 | Page 1 of 12 |
| APPLICATION NO. | : 12/004051 | |
| DATED | : August 24, 2010 | |
| INVENTOR(S) | : Galle Brun et al. | |

It is certified that error appears in the above-identified patent and that said Letters Patent is hereby corrected as shown below:

Title page, item 73, assignee, insert -- Paris, -- before -- (FR) --.

Claim 1, col. 36, line 38, "1 to 30 atoms" should read -- 1 to 30 carbon atoms --.

Claim 4, col. 37, line 5, "alky1" should read -- alkyl --.

Claim 4, col. 37, line 5, insert -- atoms -- between -- carbon -- and "and".

Claim 5, col. 37, lines 9-13 " $\frac{R_m R' SiO_{(3-m)}}{2}$ I " should read -- $\frac{R_n SiO_{(4-n)}}{2}$ II --.

Claim 13, replace the attached ten pages of structures

| Dye | Chemical structure | Log P |
|---|---|---|
| Solvent Black 3 | 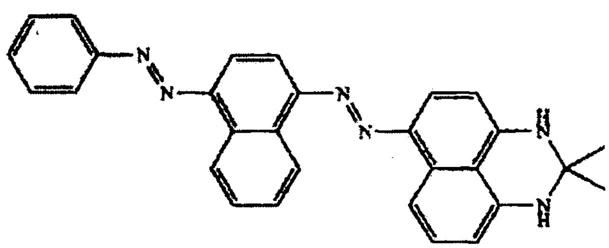 | 8.81 |

Signed and Sealed this
Twenty-first Day of February, 2012

David J. Kappos
*Director of the United States Patent and Trademark Office*

| Dye | Chemical structure | Log P |
|---|---|---|
| Solvent Blue 104 | 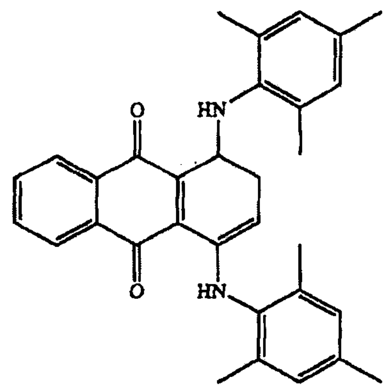 | 8.26 |
| Disperse Blue 134 | 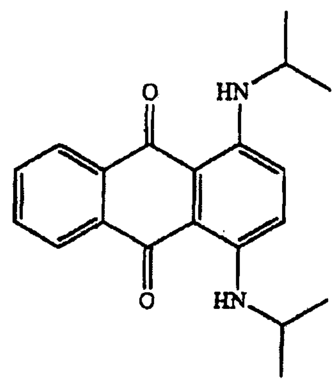 | 6.07 |
| Solvent Blue 14 | | 8.18 |
| Solvent Blue 14 | | 8.18 |

| Dye | Chemical structure | Log P |
|---|---|---|
| Disperse Blue 14 | 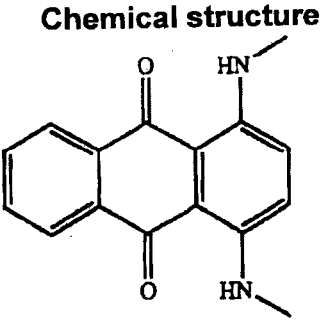 | 4.25 |
| Solvent Red 2 | 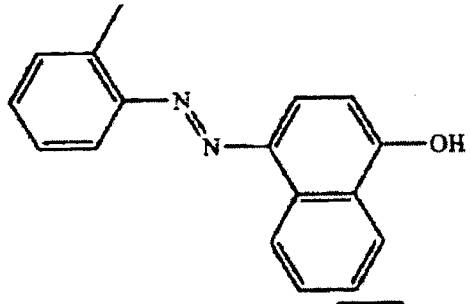 | 5.35 |
| Solvent Brown 5 | 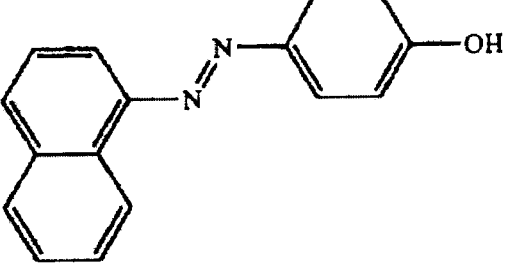 | 5.98 |
| Solvent Green 5 | 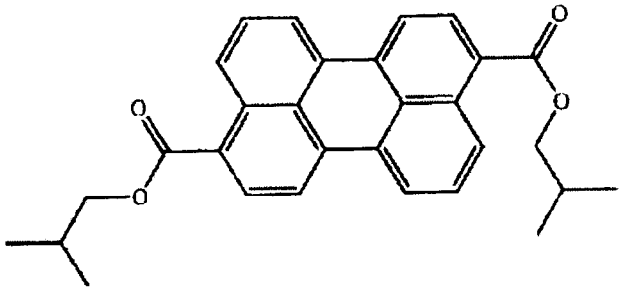 | 8.55 |

| Dye | Chemical structure | Log P |
|---|---|---|
| Solvent Orange 2 | 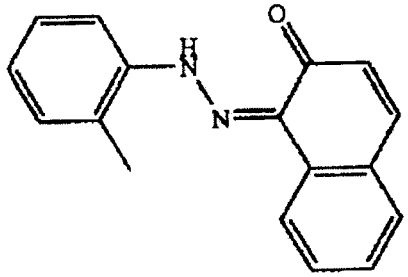 | 3.86 |
| Solvent Orange 1 | 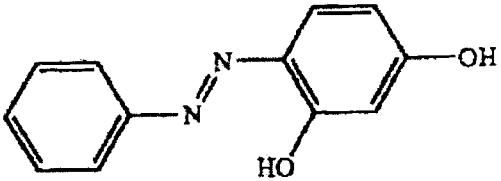 | 3.85 |
| Disperse Orange 24 | 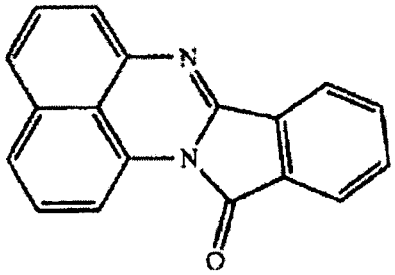 | 3.21 |
| Solvent Orange 63 | 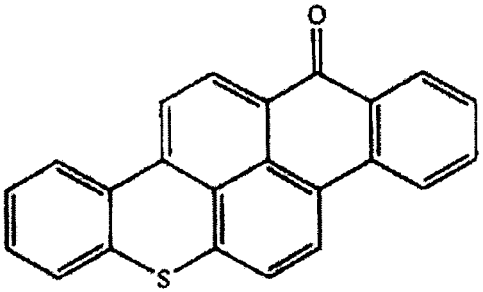 | 7.02 |
| Solvent Red 49 | 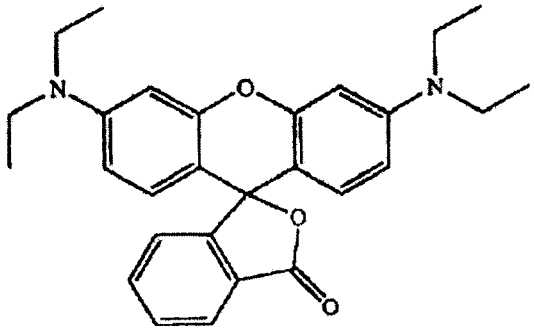 | 6.63 |

| Dye | Chemical structure | Log P |
|---|---|---|
| Solvent Red 1 | 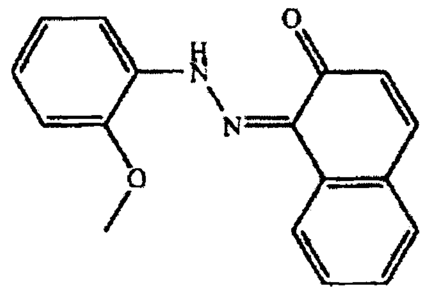 | 3.39 |
| Solvent Red 26 | 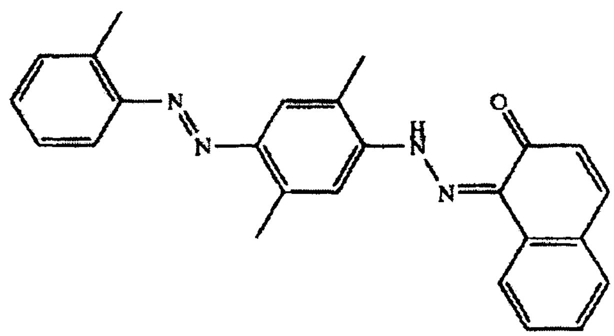 | 7.07 |
| Solvent Red 27 | 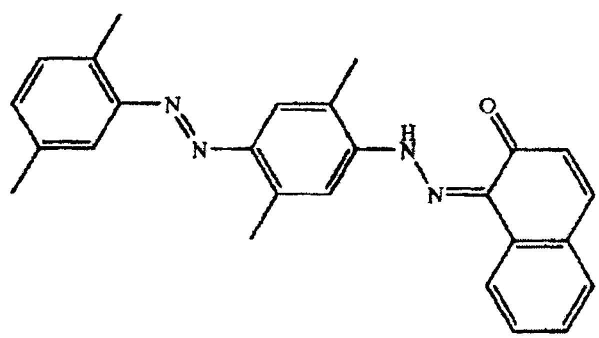 | 7.62 |
| Solvent Red 18 | 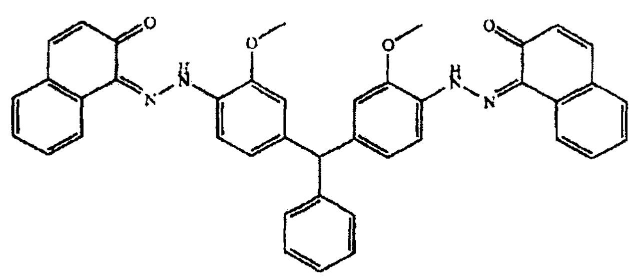 | 8.16 |

| Dye | Chemical structure | Log P |
|---|---|---|
| Solvent Red 23 | 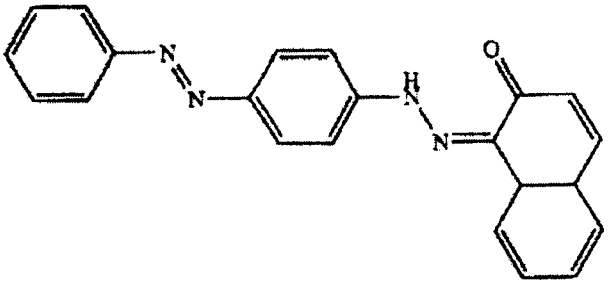 | 5.58 |
| Solvent Red 4 | 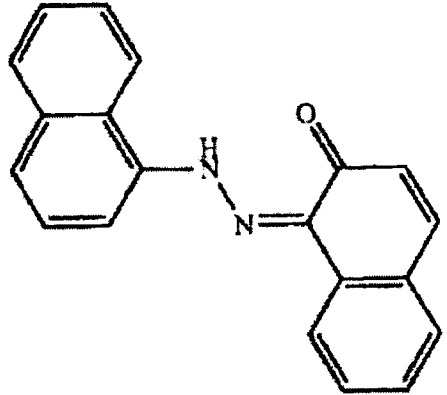 | 4.48 |
| Solvent Orange 7 | 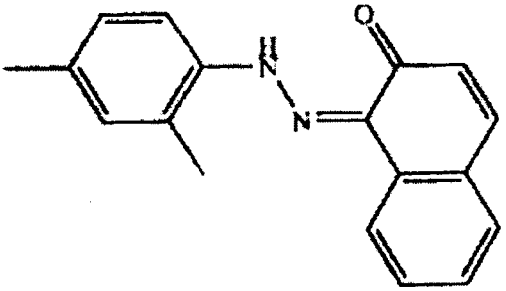 | 4.40 |
| Disperse Blue 72 | 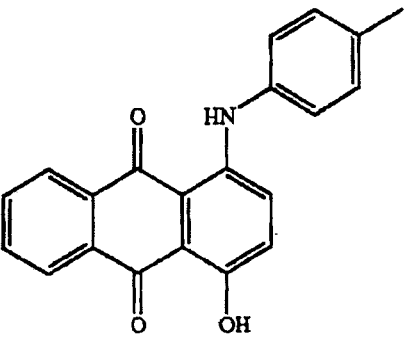 | 6.24 |

| Dye | Chemical structure | Log P |
|---|---|---|
| Disperse Violet 26 | 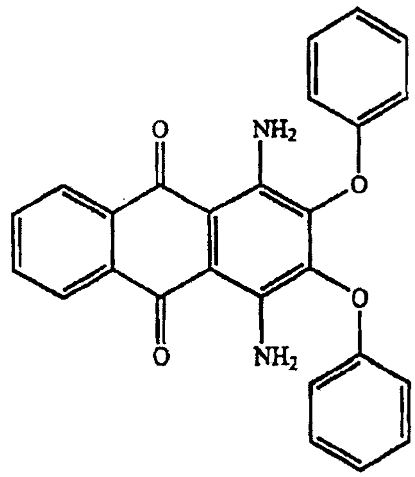 | 5.19 |
| Disperse Yellow 16 | 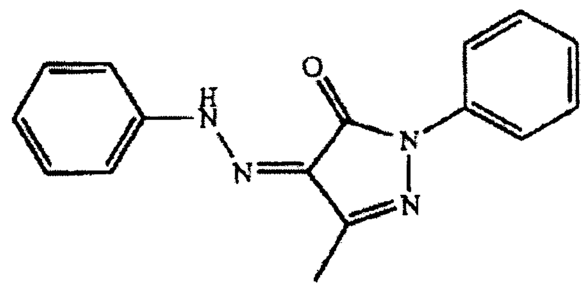 | 3.89 |
| Disperse Yellow 82 | 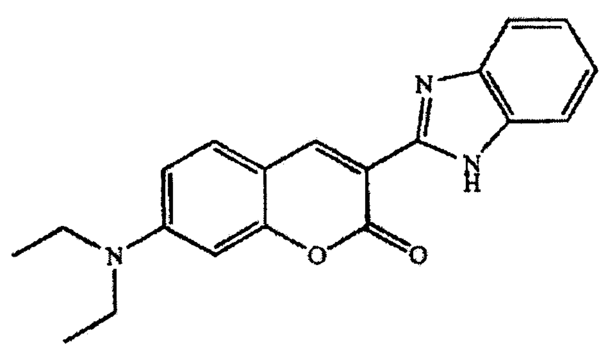 | 3.68 |
| Disperse Yellow 54 | 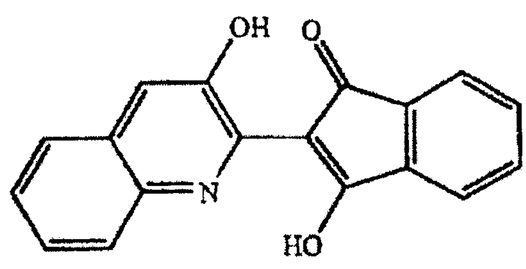 | 4.76 |

| Dye | Chemical structure | Log P |
|---|---|---|
| Solvent Yellow 29 | 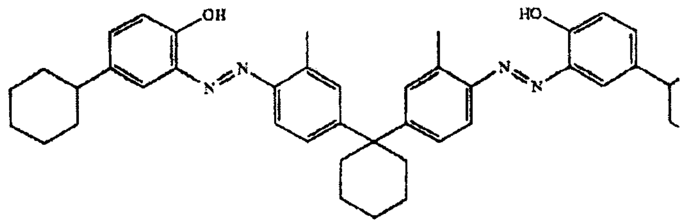 | 17.37 |
| Solvent Yellow 163 | 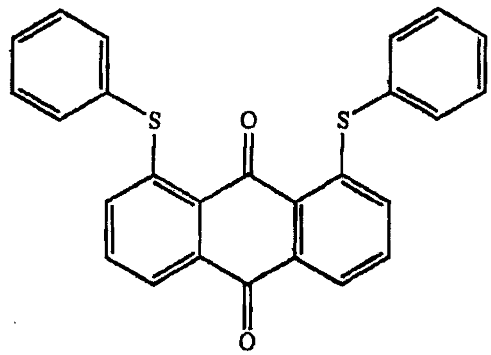 | 7.94 |
| Solvent Yellow 3 | 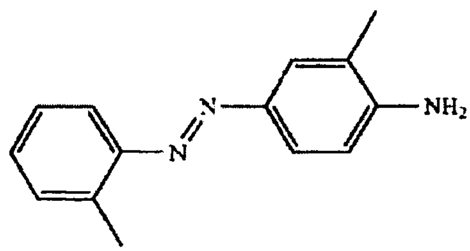 | 4.29 |
| Solvent Yellow 56 | 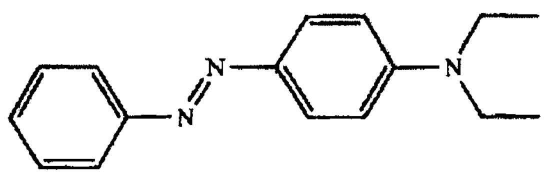 | 5.27 |
| Solvent Yellow 18 | 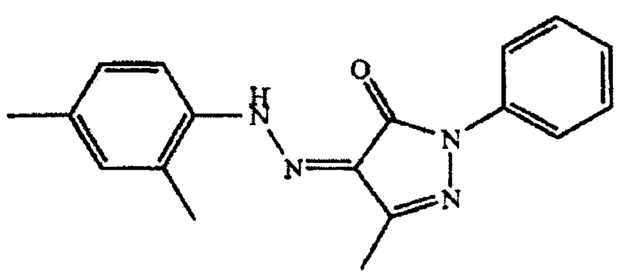 | 4.98 |

| Dye | Chemical structure | Log P |
|---|---|---|
| Solvent Yellow 98 | 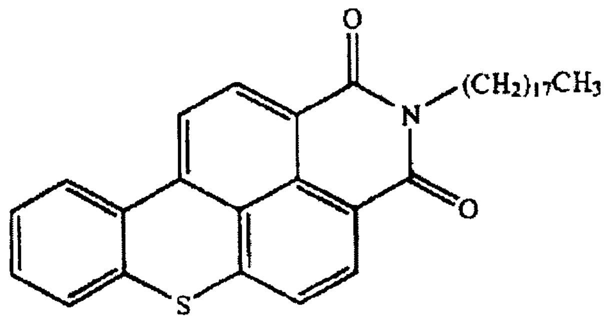 | 4.5 |
| Solvent Yellow 12 | 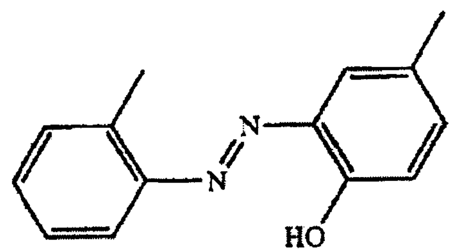 | 5.43 |
| Solvent Yellow 14 | 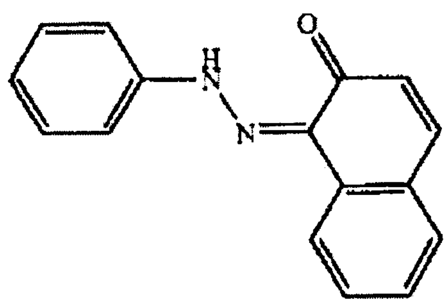 | 3.31 |
| Disperse Red 13 | 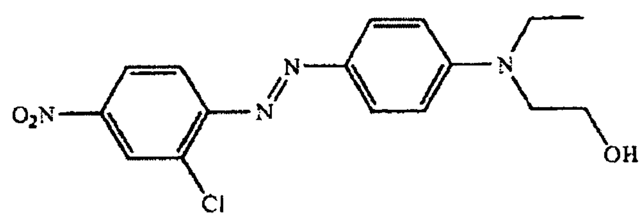 | 5.22 |
| Disperse Green 9 | 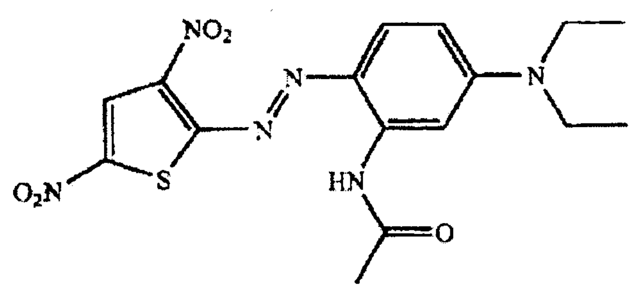 | 4.23 |

| Dye | Chemical structure | Log P |
|---|---|---|
| Disperse Blue 148 | 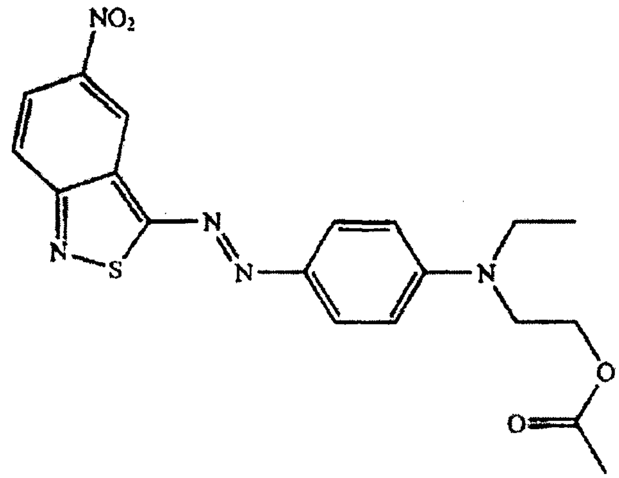 | 4.81 |
| Disperse Violet 63 | 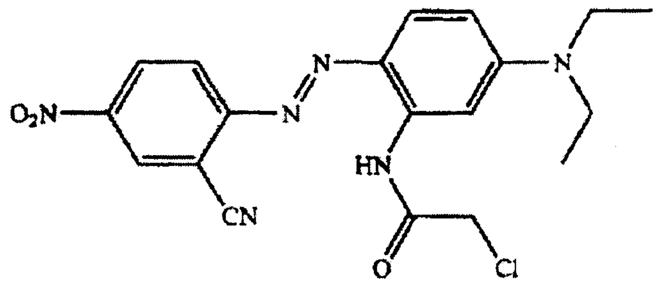 | 5.30 |
| Disperse Blue 60 | 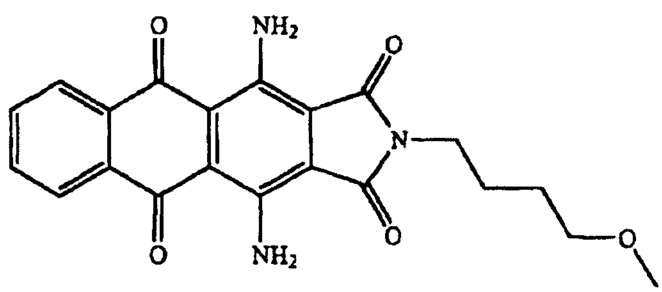 | 3.38 |
| Solvent Orange 15 | 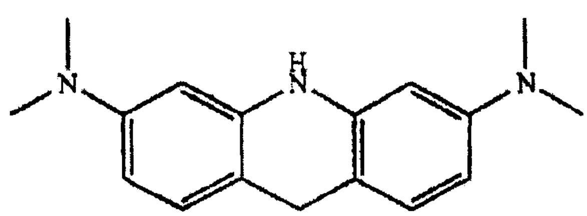 | 3.90 |

| Dye | Chemical structure | Log P |
|---|---|---|
| Solvent Blue 104 | 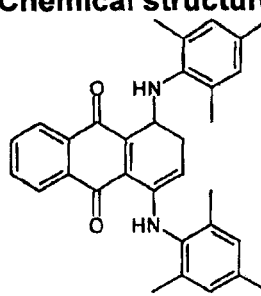 | 8.26 |
| Disperse Blue 134 | 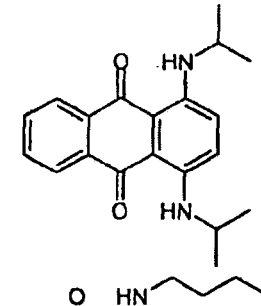 | 6.07 |
| Solvent Blue 14 | 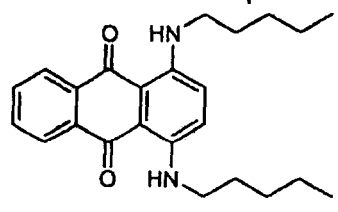 | 8.18 |
| Disperse Blue 14 | 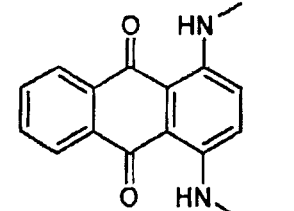 | 4.25 |
| Disperse Blue 72 | 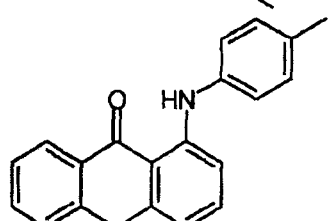 | 6.24 |

| Dye | Chemical structure | Log P |
|---|---|---|
| Disperse Violet 26 | 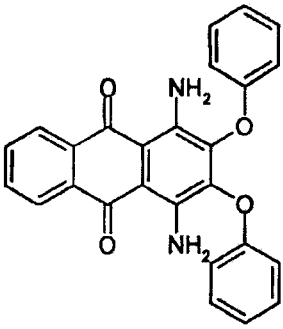 | 5.19 |
| Solvent Yellow 163 | 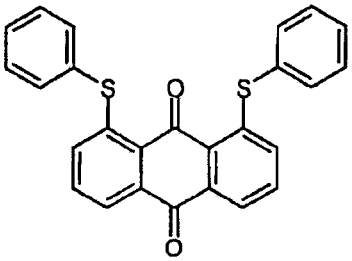 | 7.94 |
| Disperse Blue 60 | 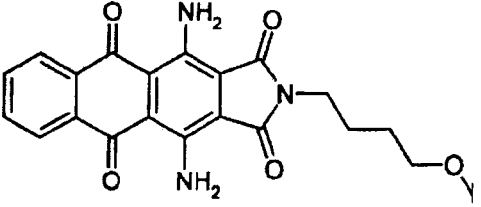 | 3.38 |
Claim 18, col. 51, line 5, delete "a" before -- formula --.
Claim 19, col. 52, line 10, "1 to 30 atoms" should read -- 1 to 30 carbon atoms --.